United States Patent
LaNeve et al.

(10) Patent No.: US 11,058,556 B2
(45) Date of Patent: Jul. 13, 2021

(54) MULTIMODAL ABRADING DEVICE FOR FUSING A SACROILIAC JOINT

(71) Applicant: Pain TEQ, LLC, Tampa, FL (US)

(72) Inventors: Sean LaNeve, Tampa, FL (US);
Charles Girsch, Tampa, FL (US);
Chris Girsch, Tampa, FL (US)

(73) Assignee: Pain TEQ, LLC, Tampa, FL (US)

( * ) Notice: Subject to any disclaimer, the term of this patent is extended or adjusted under 35 U.S.C. 154(b) by 0 days.

(21) Appl. No.: 17/063,609

(22) Filed: Oct. 5, 2020

(65) Prior Publication Data

US 2021/0100661 A1 Apr. 8, 2021

Related U.S. Application Data

(63) Continuation-in-part of application No. 16/851,840, filed on Apr. 17, 2020.

(Continued)

(51) Int. Cl.
*A61F 2/46* (2006.01)
*A61B 17/16* (2006.01)
*A61B 17/00* (2006.01)

(52) U.S. Cl.
CPC ........ *A61F 2/4611* (2013.01); *A61B 17/1671* (2013.01); *A61B 2017/00477* (2013.01); *A61F 2002/4681* (2013.01)

(58) Field of Classification Search
CPC ............... A61F 2/4611; A61B 17/1671; A61B 17/1659
See application file for complete search history.

(56) References Cited

U.S. PATENT DOCUMENTS

| 4,569,338 A | 2/1986 | Edwards |
| 5,334,205 A | 8/1994 | Cain |

(Continued)

FOREIGN PATENT DOCUMENTS

| AU | 726979 | 10/1998 |
| AU | 756550 | 5/2002 |

(Continued)

OTHER PUBLICATIONS

Steven P. Cohen, MD, Sacroiliac Joint Pain: A Comprehensive Review of anatomy, Diagnosis, and Treatment, Review Article, Apr. 27, 2005, 1440-1453, vol. 101, International Anesthesia Research Society, United States.

(Continued)

*Primary Examiner* — Andrew Yang
(74) *Attorney, Agent, or Firm* — Stephen E. Kelly; Thomas J. Banks; Hill Ward Henderson, P.A.

(57) ABSTRACT

A multimodal abrading device for preparing a sacroiliac joint ("SI Joint") to receive a graft implant. The abrading device comprises an abrading head having abrading surfaces on a first pair of opposing sides, the abrading surfaces configured for decorticating the cortical bone of the SI Joint. The abrading head further comprises an open tip having a cutting edge configured to cut bone tissue in the SI Joint. The abrading device further comprises a slide hammer assembly at a proximal end of the abrading device, the slide hammer assembly having a released position that enables operation of the slide hammer assembly, and a locked position that prohibits operation of the slide hammer assembly.

19 Claims, 25 Drawing Sheets

US 11,058,556 B2

Page 2

Related U.S. Application Data

(60) Provisional application No. 62/910,913, filed on Oct. 4, 2019.

(56) References Cited

U.S. PATENT DOCUMENTS

| | | | |
|---|---|---|---|
| 5,722,978 | A | 3/1998 | Jenkins, Jr. |
| 6,080,155 | A | 6/2000 | Michelson |
| 6,371,988 | B1 | 4/2002 | Pafford et al. |
| 6,436,098 | B1 | 8/2002 | Michelson |
| 6,648,917 | B2 | 11/2003 | Gerbec et al. |
| 6,652,533 | B2 * | 11/2003 | O'Neil ............... A61F 2/4611 606/100 |
| 6,770,074 | B2 | 8/2004 | Michelson |
| 6,846,327 | B2 | 1/2005 | Khandkar et al. |
| 7,018,416 | B2 | 3/2006 | Hanson et al. |
| 7,125,425 | B2 | 10/2006 | Foley et al. |
| 7,229,477 | B2 | 6/2007 | Biscup |
| 7,648,509 | B2 | 1/2010 | Stark |
| 8,021,392 | B2 | 9/2011 | Petersen |
| 8,025,684 | B2 | 9/2011 | Garcia-Bengochea et al. |
| 8,128,700 | B2 | 3/2012 | Delurio et al. |
| 8,157,865 | B2 | 4/2012 | Hochschuler et al. |
| 8,162,981 | B2 | 4/2012 | Vestgaarden |
| 8,197,513 | B2 | 6/2012 | Fisher et al. |
| 8,221,503 | B2 | 7/2012 | Garcia et al. |
| 8,348,950 | B2 | 1/2013 | Assell et al. |
| 8,403,991 | B2 | 3/2013 | Ullrich, Jr. et al. |
| 8,551,171 | B2 | 10/2013 | Johnson et al. |
| 8,579,912 | B2 | 11/2013 | Isaza et al. |
| 8,623,053 | B2 | 1/2014 | Vestgaarden |
| 8,740,912 | B2 | 6/2014 | Stark |
| 8,882,818 | B1 | 11/2014 | Vestgaarden |
| 8,945,224 | B2 | 2/2015 | Trieu |
| 8,961,571 | B2 | 2/2015 | Lee et al. |
| 8,979,928 | B2 | 2/2015 | Donner |
| 9,017,407 | B2 | 4/2015 | Donner |
| 9,101,371 | B2 | 8/2015 | Assell et al. |
| 9,119,732 | B2 | 9/2015 | Schifano et al. |
| 9,186,155 | B2 | 11/2015 | Katzman et al. |
| 9,241,798 | B2 | 1/2016 | Petersen |
| 9,247,943 | B1 * | 2/2016 | Kleiner ............... A61B 17/1671 |
| 9,375,243 | B1 | 6/2016 | Vestgaarden |
| 9,421,109 | B2 | 8/2016 | Donner |
| 9,451,986 | B2 | 9/2016 | Stoffman |
| 9,492,284 | B2 | 11/2016 | Ginn et al. |
| 9,662,128 | B2 | 5/2017 | Reiley |
| 9,668,781 | B2 | 6/2017 | Stark |
| 9,700,356 | B2 | 7/2017 | Donner et al. |
| 9,757,154 | B2 | 9/2017 | Donner et al. |
| 9,795,396 | B2 | 10/2017 | Donner |
| 9,801,732 | B2 | 10/2017 | Chin et al. |
| 9,808,346 | B2 | 11/2017 | Stark |
| 9,833,321 | B2 | 12/2017 | Rindal |
| 9,883,874 | B1 | 2/2018 | Vestgaarden |
| 9,895,176 | B2 | 2/2018 | Vestgaarden |
| 9,949,843 | B2 | 4/2018 | Reiley et al. |
| 10,004,547 | B2 | 6/2018 | Reiley |
| 10,070,970 | B2 | 9/2018 | Lynn et al. |
| 10,136,932 | B2 | 11/2018 | Freese |
| 10,149,764 | B2 | 12/2018 | Stark |
| 10,166,033 | B2 | 1/2019 | Reiley et al. |
| 10,194,962 | B2 | 2/2019 | Schneider et al. |
| 10,201,427 | B2 | 2/2019 | Mauldin |
| 10,206,739 | B2 | 2/2019 | Godara et al. |
| 10,245,044 | B2 | 2/2019 | Petersen |
| 10,219,841 | B1 | 3/2019 | Compton |
| 10,219,912 | B2 | 3/2019 | Suh et al. |
| 10,245,158 | B2 | 4/2019 | Song |
| 10,265,176 | B2 | 4/2019 | Donner et al. |
| 10,292,720 | B2 | 5/2019 | Donner |
| 10,314,710 | B2 | 6/2019 | Donner et al. |
| 10,321,945 | B2 | 6/2019 | Schifano et al. |
| 10,357,368 | B2 | 7/2019 | Aksu |
| 10,363,140 | B2 | 7/2019 | Mauldin et al. |
| 10,426,539 | B2 | 10/2019 | Schifano et al. |
| 10,492,802 | B2 * | 12/2019 | Donner ............... A61B 17/144 |
| 10,555,818 | B2 | 2/2020 | McConnell et al. |
| 10,646,258 | B2 | 5/2020 | Donner et al. |
| 10,682,150 | B2 | 6/2020 | Stark |
| 10,736,752 | B1 | 8/2020 | Schifano et al. |
| 10,744,003 | B2 | 8/2020 | Ryan et al. |
| 10,751,196 | B1 | 8/2020 | Schifano et al. |
| 10,765,532 | B2 | 9/2020 | Ashleigh et al. |
| 10,779,958 | B2 | 9/2020 | Lines |
| 10,820,917 | B2 | 11/2020 | Sharifi-Mehr et al. |
| D905,232 | S | 12/2020 | Schifano et al. |
| 2001/0031967 | A1 | 10/2001 | Nicholson et al. |
| 2002/0143400 | A1 | 10/2002 | Biscup |
| 2005/0080422 | A1 * | 4/2005 | Otte ............... A61F 2/447 606/85 |
| 2005/0240195 | A1 | 10/2005 | Axelson, Jr. et al. |
| 2006/0054171 | A1 | 3/2006 | Dall |
| 2006/0089633 | A1 | 4/2006 | Bleich et al. |
| 2006/0178673 | A1 | 8/2006 | Curran et al. |
| 2007/0156241 | A1 | 7/2007 | Reiley et al. |
| 2008/0009861 | A1 | 1/2008 | Stark |
| 2008/0154374 | A1 | 6/2008 | Labrom |
| 2008/0249569 | A1 | 10/2008 | Waugh et al. |
| 2009/0024174 | A1 | 1/2009 | Stark |
| 2009/0076551 | A1 | 3/2009 | Petersen |
| 2009/0099610 | A1 | 4/2009 | Johnson et al. |
| 2009/0216238 | A1 | 8/2009 | Stark |
| 2009/0259261 | A1 | 10/2009 | Reiley |
| 2009/0312763 | A1 | 12/2009 | McCormack et al. |
| 2011/0098817 | A1 | 4/2011 | Eckhardt |
| 2011/0184518 | A1 | 7/2011 | Trieu |
| 2011/0238181 | A1 | 9/2011 | Trieu |
| 2011/0264229 | A1 | 10/2011 | Donner |
| 2012/0083883 | A1 | 4/2012 | Ginn |
| 2012/0259365 | A1 | 10/2012 | Richelsoph |
| 2012/0277801 | A1 | 11/2012 | Marik et al. |
| 2013/0006368 | A1 | 1/2013 | Walsh et al. |
| 2013/0173004 | A1 | 7/2013 | Greenhalgh et al. |
| 2013/0218215 | A1 | 8/2013 | Ginn et al. |
| 2014/0031935 | A1 | 1/2014 | Donner et al. |
| 2014/0081279 | A1 | 3/2014 | Kleiner et al. |
| 2014/0088711 | A1 | 3/2014 | Kingsley et al. |
| 2014/0207191 | A1 | 7/2014 | Kornel |
| 2014/0277204 | A1 | 9/2014 | Sandhu |
| 2015/0012097 | A1 | 1/2015 | Ibarra et al. |
| 2015/0025534 | A1 | 1/2015 | Gordan et al. |
| 2015/0073552 | A1 | 3/2015 | To et al. |
| 2015/0112444 | A1 | 4/2015 | Aksu |
| 2015/0230937 | A1 | 8/2015 | Voellmicke |
| 2015/0250611 | A1 | 9/2015 | Schifano et al. |
| 2015/0250612 | A1 | 9/2015 | Schifano et al. |
| 2015/0328012 | A1 | 11/2015 | Hansell et al. |
| 2016/0030191 | A1 | 2/2016 | McLuen et al. |
| 2016/0175113 | A1 | 6/2016 | Lins |
| 2016/0310197 | A1 | 10/2016 | Black et al. |
| 2017/0245999 | A1 | 8/2017 | Ginn et al. |
| 2018/0036017 | A1 | 2/2018 | Donner et al. |
| 2018/0092748 | A1 | 4/2018 | Donner et al. |
| 2018/0303624 | A1 | 10/2018 | Shoshtaev |
| 2019/0021868 | A1 | 1/2019 | Ludwig et al. |
| 2019/0083271 | A1 | 3/2019 | Donner et al. |
| 2019/0090888 | A1 | 3/2019 | Sand et al. |
| 2019/0133613 | A1 | 5/2019 | Reiley et al. |
| 2019/0262010 | A1 | 8/2019 | Cerundolo et al. |
| 2019/0336292 | A1 | 11/2019 | Aksu |
| 2019/0343640 | A1 | 11/2019 | Donner et al. |
| 2020/0029979 | A1 | 1/2020 | Donner et al. |
| 2020/0093612 | A1 | 3/2020 | Blain et al. |
| 2020/0138452 | A1 | 5/2020 | Gatrell et al. |
| 2020/0138589 | A1 | 5/2020 | Abbasi |
| 2020/0179135 | A1 | 6/2020 | Castro |
| 2020/0253619 | A1 | 8/2020 | Gregory |
| 2020/0315811 | A1 | 10/2020 | Cryder et al. |

(56) References Cited

U.S. PATENT DOCUMENTS

2020/0390566 A1 12/2020 Murray et al.
2021/0015502 A1 1/2021 Sharifi-Mehr et al.

FOREIGN PATENT DOCUMENTS

| CN | 110123436 | 8/2019 |
|----|-----------|--------|
| FR | 2727004 | 5/1996 |
| WO | WO/2017066443 | 4/2017 |
| WO | WO/2018195406 | 10/2018 |
| WO | WO/2019137626 | 7/2019 |

OTHER PUBLICATIONS

K. A. Giannikas, A. M. Khan, M.T. Karski, H. A. Maxwell, Sacroiliac joint fusion for chronic pain: a simple technique avoiding the use of metalwork, Journal, Nov. 28, 2003, 253-256, vol. 13, Springer-Verlag, Greece.

Captiva Spine, TransFasten Posterior Sacroiliac (SI) Joint Fusion System, available at, https://transfasten.captivaspine.com/si-joint-surgeon-providers/, last visited on Jan. 5, 2021.
United Stated Patent and Trademark Office, Office Action for U.S. Appl. No. 17/063,616, dated Jan. 4, 2021.
International Search Report and Written Opinion for International. Appl. No. PCT/US20/54299, dated Jan. 8, 2021.
International Search Report and Written Opinion for International. Appl. No. PCT/US20/54308, dated Jan. 8, 2021.
International Search Report and Written Opinion for International. Appl. No. PCT/US20/54290, dated Jan. 21, 2021.
U.S. Appl. No. 16/851,840, filed Apr. 17, 2020, Sean LaNeve Charles Girsch Chris Girsch.
U.S. Appl. No. 17/063,613, filed Oct. 5, 2020 Sean LaNeve Charles Girsch Chris Girsch.
U.S. Appl. No. 17/063,616, filed Oct. 5, 2020, Sean LaNeve Charles Girsch Chris Girsch.
United States Patent and Trademark Office, Notice of Allowance for U.S. Appl. No. 17/063,613, dated Feb. 3, 2021.
International Search Report and Written Opinion for International. Appl. No. PCT/US20/54312, dated Feb. 8, 2021.

* cited by examiner

MULTIMODAL ABRADING DEVICE FOR FUSING A SACROILIAC JOINT

CROSS-REFERENCE TO RELATED APPLICATION

Pursuant to 35 U.S.C. §§ 119(e) and 120, this application:
(i) is a continuation-in-part of U.S. patent application Ser. No. 16/851,840, filed on Apr. 17, 2020, which claims the benefit of U.S. Provisional Patent Application Ser. No. 62/910,913, filed on Oct. 4, 2019; and
(ii) claims the benefit of U.S. Provisional Patent Application Ser. No. 62/910,913, filed on Oct. 4, 2019,
the entire contents of each of which are incorporated herein by this reference.

BACKGROUND

(1) Field of Endeavor

The present invention relates generally to the field of sacroiliac joint fusion procedures, and more particularly, to a unique abrading device for preparing the sacroiliac joint for receiving a graft implant.

(2) Description of Related Art

The sacroiliac joint ("SI Joint") is located at the interface between the sacrum and ilium bones in a human's pelvic area. The SI Joint includes strong ligaments that permit only slight movement between the sacrum and the ilium. The sacrum is connected to the base of the spine, and each ilium is connected to the top of the leg and hip area. Thus, the SI Joint is the interface between a human's upper body and lower body.

Dysfunction in the SI Joint is a common problem of back pain. In fact, over 25% of back pain is caused by SI Joint dysfunction. Even a properly functioning SI Joint can become painful after certain types of spinal procedures. For example, over 75% of lumbar fusion surgeries lead to SI Joint pain. Often, SI Joint pain or dysfunction is addressed by fusing the SI Joint, and many past procedures exist for doing so. Past SI Joint fusion procedures involve installation of complex implant devices, such as bone anchors, fusion devices, and multi-component implants. These procedures involve complex devices, such as drills and drill bits, and multi-component dilators, braces, and anchor installation devices. As a result, fusion procedures using these devices are complex and time consuming, often leading to suboptimal results.

The present set of instruments seeks to overcome these problems by providing a streamlined system and procedure for installing an allograft implant in the SI Joint, without using a drill, drill bits, or other rotary cutting instruments.

Another complication of SI Joint fusion is that promoting bone fusion often involves decorticating the cortical bone inside the SI Joint. This decortication is accomplished with a broach, a rasp, or a similar abrading device. These abrading devices often become lodged inside the SI Joint during the decortication process. When the abrading device becomes lodged, counter pressure cannot be applied to the patient to counteract the pull-out force needed to dislodge the abrading device. Any such counter pressure applied to the patient could result in injury to the patient or damage to the tissue surrounding the surgical site. A past solution is to attach a separate slap hammer, or slide hammer, to the abrading device such that pull-out forces can be applied to the abrading device without the need for applying any counter pressure to the patient or to any other object. However, past slide hammer assemblies are cumbersome to operate, difficult to attach to the abrading device, and difficult to operate. They also complicate the instrumentation needed to perform the SI Joint fusion procedure.

The present set of instruments seeks to overcome these problems by providing a slide hammer integrated into the abrading device in a single tool.

SUMMARY OF THE PREFERRED EMBODIMENTS

In the preferred embodiment, the system and instrumentation described herein comprises a working channel, a joint locator, an abrading device, and an implant inserter. The working channel has an insertion end and a working end, and a channel extending therebetween. The working channel provides a working passage for insertion of the other instruments of the system, and for delivery of the implant to the SI Joint. The insertion end has a pair of arms for providing engagement of the SI Joint and distraction of tissue surrounding the insertion end. The insertion end further comprises a first iliac contour and a first sacral contour, both of which are defined by the contour between the insertion arms and the body of the working channel. The inside surface of the working channel has an alignment means comprising a groove, recess, channel, indent, or the like for receiving and engaging a ridge, rib, detent, or other protrusion on the mating instrument that is keyed to the alignment means. In one embodiment, the working channel further comprises a channel collar for receiving mating components of the joint locator, abrading device, or implant inserter in an abutting engagement.

The joint locator has an insertion end and a handle. The insertion end comprises a penetration tip for penetrating the soft tissue in proximity to the SI Joint. A leading edge of the penetration tip may comprise, in whole or in part, a blade or chisel component to promote this penetration. Alternately, the penetration tip may be rounded or dull so that it does not inadvertently penetrate the sacrum or ilium in the event that the joint locator is misaligned during insertion. The joint locator insertion end comprises a second iliac contour and a second sacral contour. The outside surface of the joint locator has a keying means for engagement with the alignment means of the working channel, the keying means comprising a ridge, rib, detent, or other protrusion on the outside surface of the joint locator capable of engaging the alignment means.

The abrading device comprises a hammer sleeve at a proximate end, an abrading head at a distal end, and a keying means that is similar to the joint locator keying means of the joint locator. In the preferred embodiment, the abrading device further comprises a slap hammer assembly, or slide hammer assembly. In one embodiment, the slide hammer assembly comprises a base connected to a shaft, and a releasing means that releasably connects a hammer sleeve to the base. The released hammer sleeve is configured for sliding engagement along the shaft. To operate the slide hammer assembly, the hammer sleeve is disengaged from the base, placing the slide hammer assembly in its released position. This released position enables the hammer sleeve to slide freely along the shaft. The hammer sleeve is pulled until a diaphragm inside the hammer sleeve engages a stop end of the shaft, thereby causing an impact that delivers the slide hammer force.

The implant inserter comprises a handle and an implant insertion end. The implant insertion end has a pair of tines for holding the implant during the process of inserting the implant into the SI Joint. The implant inserter further comprises an inserter keying means, which is similar to the keying means of the joint locator.

DETAILED DESCRIPTION OF THE PREFERRED EMBODIMENTS

With reference to the drawings, the system and instrumentation for fusing a sacroiliac joint ("SI Joint") and the corresponding multimodal abrading device will now be described with regard for the best mode and the preferred embodiment. The embodiments disclosed herein are meant for illustration and not limitation of the invention. An ordinary practitioner will appreciate that it is possible to create many variations of the following embodiments without undue experimentation.

Figure 1:
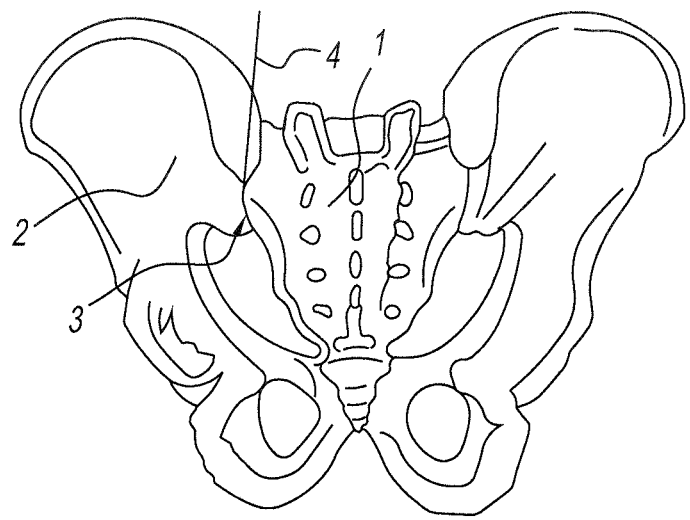
FIG. 1 shows the posterior view of a typical human pelvis.
Figure 2:
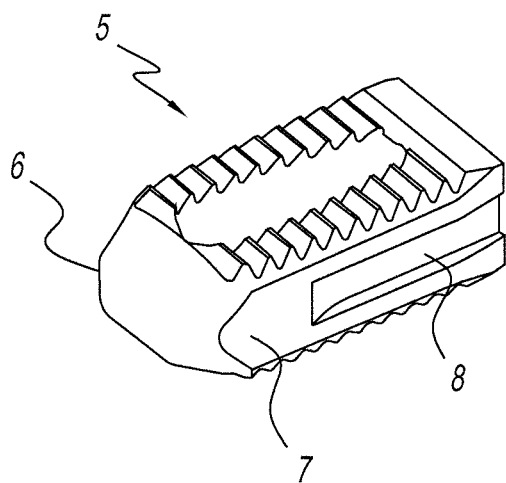
FIG. 2 is a perspective view of an embodiment of an allograft implant for insertion into the SI Joint.
Figure 3:
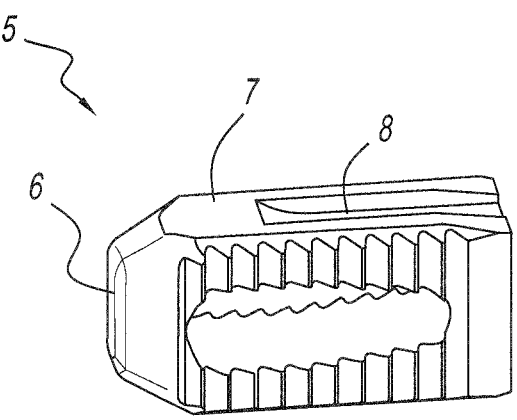
FIG. 3 shows an alternate view of one embodiment of an allograft implant.

The system and instrumentation described herein are used primarily for fusing an SI Joint 3 in the pelvis of a human. Referring to FIGS. 1-3, an allograft implant 5 is placed in the soft tissue of the SI Joint 3 between the sacrum 1 and the ilium 2 of the pelvis. For the purpose of reference, the SI Joint plane as used herein means the general plane of the SI Joint 3 as defined by the abutting surfaces of the sacrum 1 and ilium 2. The implant 5 provides a matrix for bone healing across the SI Joint, thereby fusing the sacrum 1 and ilium 2 together. In one embodiment, the implant 5 generally comprises a nose 6 and at least one pair of opposing lateral sides 7, each comprising a groove 8 that is disposed at least partially along the length of each such lateral side 7.

Figure 4:
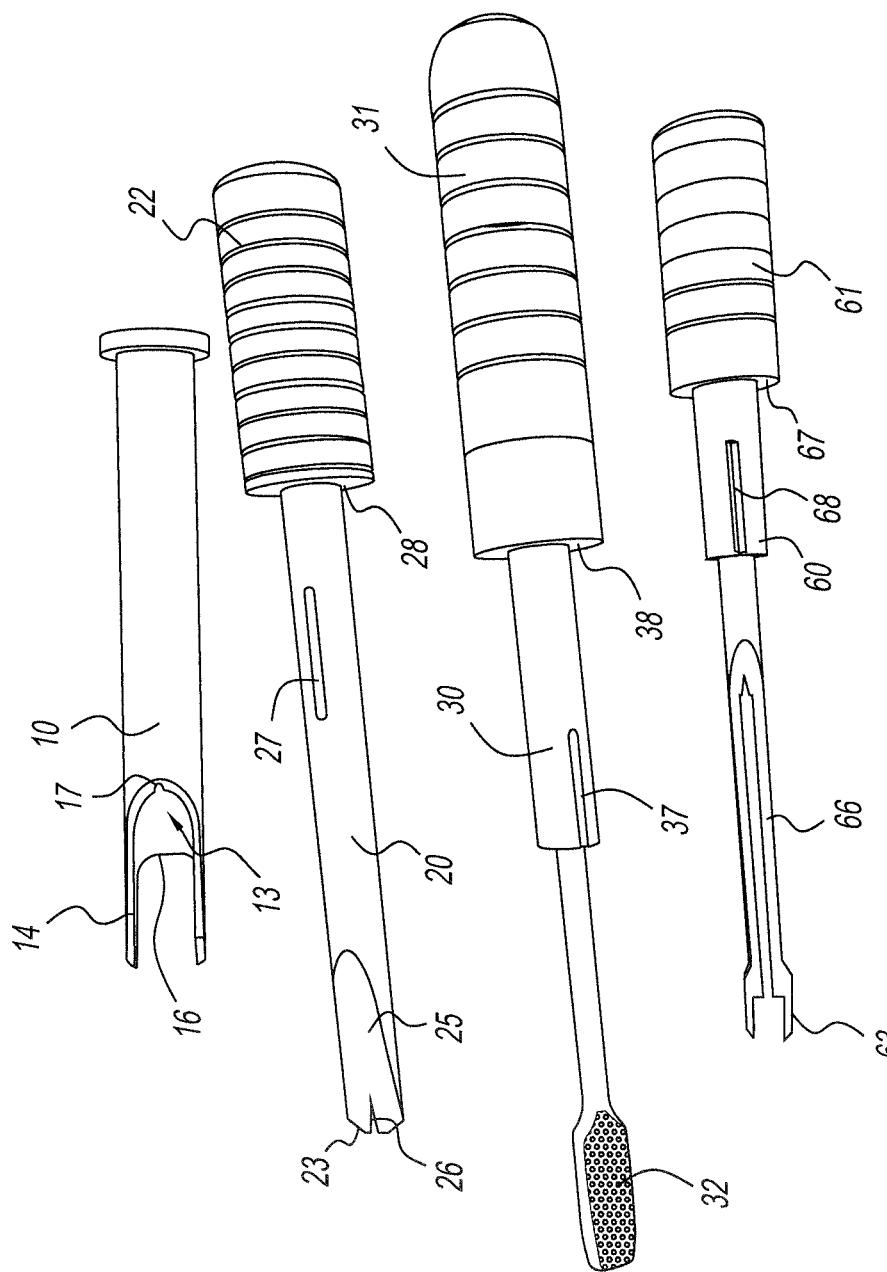
FIG. 4 shows an embodiment of the instruments in the joint fusion apparatus.
Figure 5:
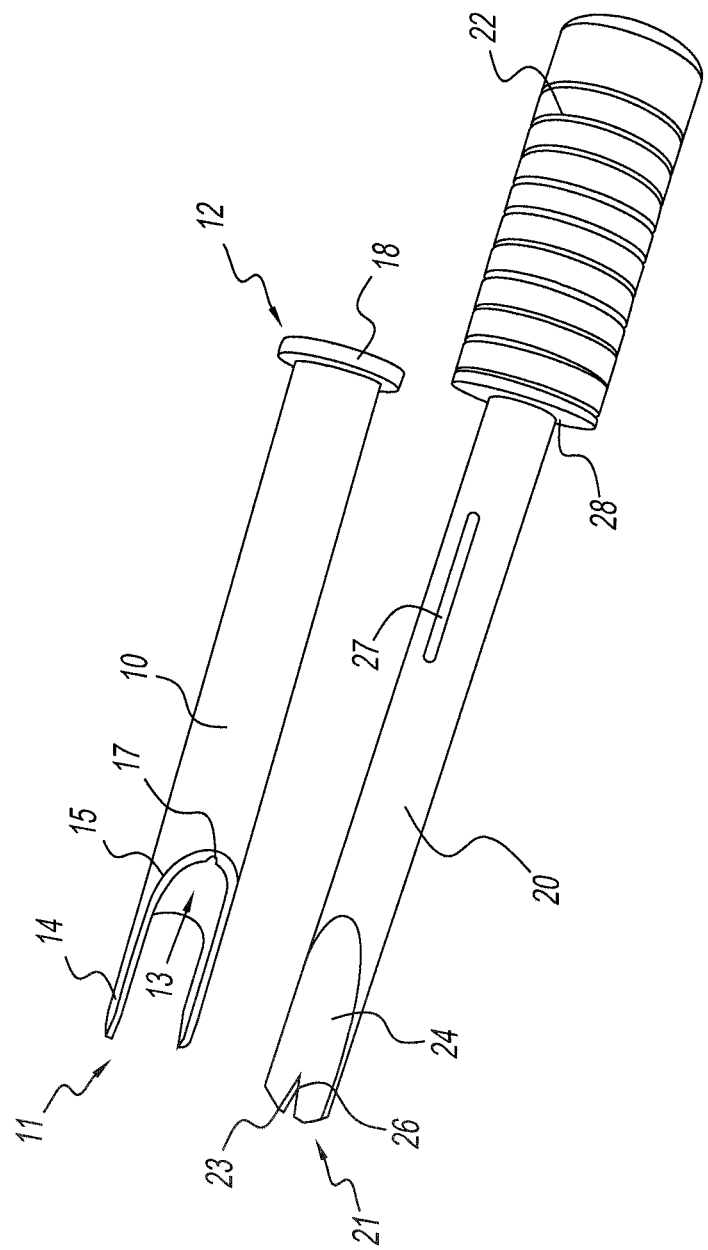
FIG. 5 shows an embodiment of the working channel and an embodiment of the joint locator.
Figure 7:
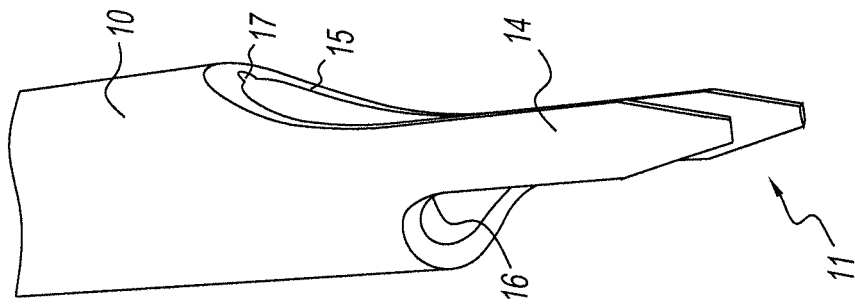
FIG. 7 shows an alternate view of the embodiment shown in FIG. 6.
Figure 6:
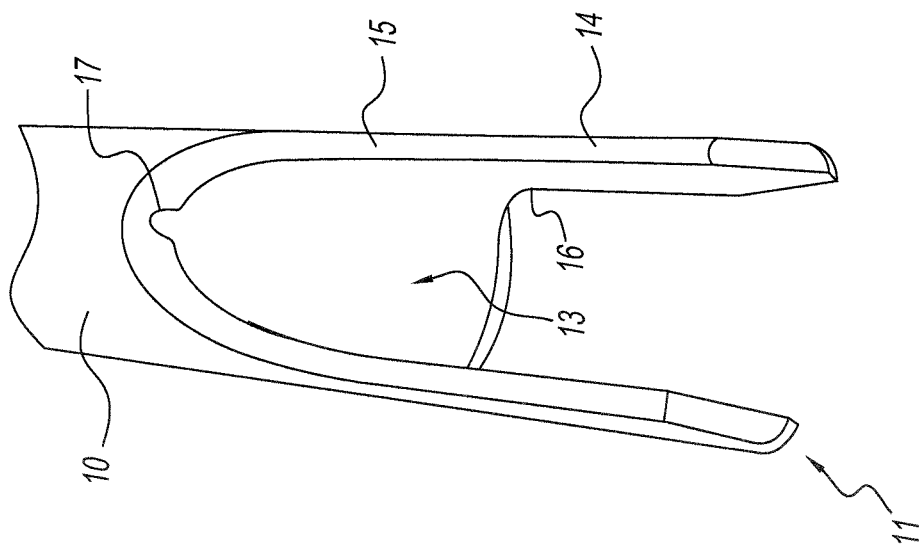
FIG. 6 shows a close up of the insertion end of one embodiment of a working channel.
Figure 9:
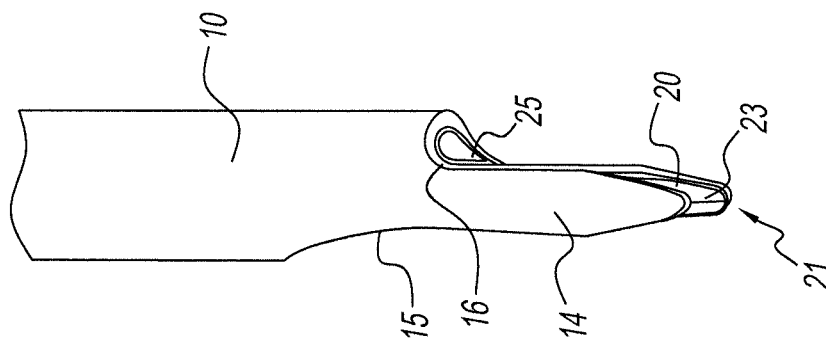
FIG. 9 is an enlarged view showing the device of FIG. 8 with the orientation reversed.
Figure 8:
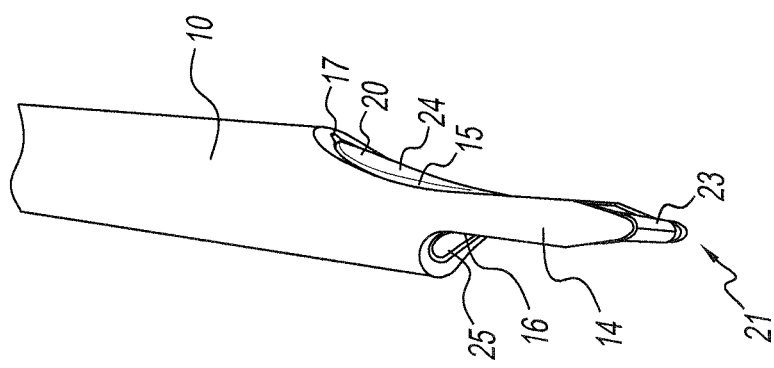
FIG. 8 is an enlarged view of the insertion end of an embodiment of the joint locator fully inserted into the working channel of FIG. 4.

Referring to FIG. 4, in one embodiment, the system comprises a working channel 10, a joint locator 20, an abrading device 30, and an implant inserter 60. Each of these instruments has a longitudinal axis along the centerline of its length. Referring to FIG. 5, the working channel 10 is a tube-like member that provides a working passage for insertion of the other instruments of the system, and for delivery of the implant 5 to the SI Joint 3. The working channel 10 is a cannula, a lumen, a sleeve, or another device suitable for providing working access of the other instruments to the SI Joint 3, as described below. The working channel 10 has an insertion end 11 and a working end 12, and a channel 13 extending therebetween. The channel 13 is a tube or bore having a cross section that is rectilinear or curvilinear. The insertion end 11 has a pair of arms 14 for providing engagement of the SI Joint 3 and distraction of tissue surrounding the insertion end 11. The arms 14 are probes, prongs, or other members protruding from the insertion end 11 of the working channel 10. Insertion of the arms 14 into the SI Joint 3, as described below, resists or prevents the working channel 10 from rotating about its longitudinal axis in relation to the SI Joint 3. The longitudinal axis generally extends along the length of the working channel 10 in proximity to the centerline of the channel 13.

The insertion end 11 of the working channel 10 is configured for seating in and against the SI Joint 3, and against the sacrum 1 and ilium 2 in particular. The insertion end 11 comprises a first iliac contour 15 and a first sacral contour 16, both of which are defined by the contour between the insertion arms 14 and the body of the working channel 10. For example, referring to FIGS. 6-9, one side of the insertion end 11 comprises the arms 14 connected to the working channel 10 via the first iliac contour 15, which is configured for abutment against the ilium 2 when the arms 14 are inserted into, and seated within, the SI Joint 3 as described below. The opposite side of the insertion end 11 comprises the arms 14 connected to the working channel 10 via the first sacral contour 16, which is configured for abutment against the sacrum 1 when the arms 14 are inserted into, and seated within, the SI Joint 3.

Figure 10:
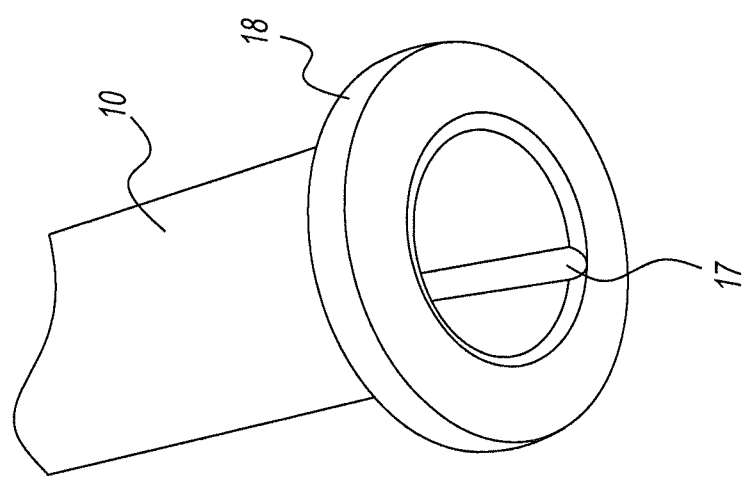
FIG. 10 shows a close up of the working end of one embodiment of a working channel.

Referring to FIGS. 5 and 10, the inside surface of the working channel 10 has a means for aligning instruments, the alignment means 17 comprising a groove, recess, channel, indent, or the like for receiving and engaging a ridge, rib, detent, or other protrusion on the mating instrument that is keyed to the alignment means 17. In one embodiment, the working channel 10 further comprises a channel collar 18 for receiving mating components of the joint locator 20, abrading device 30, or implant inserter 60 in an abutting engagement, as described below. In an embodiment of the channel collar 18, the collar further comprises an alignment means 17.

Referring to FIG. 5, the joint locator 20 has an insertion end 21 and a handle 22, or working end. The insertion end 21 comprises a penetration tip 23 for penetrating the soft tissue in proximity to the SI Joint 3. This soft tissue is the soft tissue between the surface of the patient's skin and the SI Joint 3, such as muscle tissue, and the soft tissue inside the SI Joint 3, such as cartilage and ligaments. The penetration tip 23 is configured for penetrating these types of soft tissue. For example, one embodiment of the penetration tip 23 comprises a blade or chisel component for cutting the soft tissue. A leading edge of the penetration tip 23 may comprise, in whole or in part, such a blade or chisel component. In another embodiment of the penetration tip 23, the penetration tip 23 is rounded or dull so that it does not inadvertently penetrate the sacrum 1, the ilium 2, or any other bone structure in the pelvic area in the event that the joint locator 20 is misaligned during insertion and penetration. In this embodiment, the penetration tip 23 tends to tear or rip through the soft tissue rather than slicing or cutting through it.

Referring again to FIGS. 8 and 9, the joint locator 20 insertion end 21 comprises a second iliac contour 24 and a second sacral contour 25. For example, one side of the joint locator 20 insertion end 21 comprises the second iliac contour 24, which is configured for abutment against the ilium 2 when the penetration tip 23 is inserted into the SI Joint 3, as described below. The other side of the joint locator 20 insertion end 21 comprises the second sacral contour 25, which is configured for abutment against the sacrum 1 when the penetration tip 23 is inserted into the SI Joint 3.

The outside surface of the joint locator 20 has a means for keying with the alignment means 17 of the working channel 10, the keying means 27 comprising a ridge, rib, detent, or other protrusion on the outside surface of the joint locator 20 capable of engaging the alignment means 17 to resist or prevent relative rotation between the joint locator 20 and the working channel 10.

Figure 11:
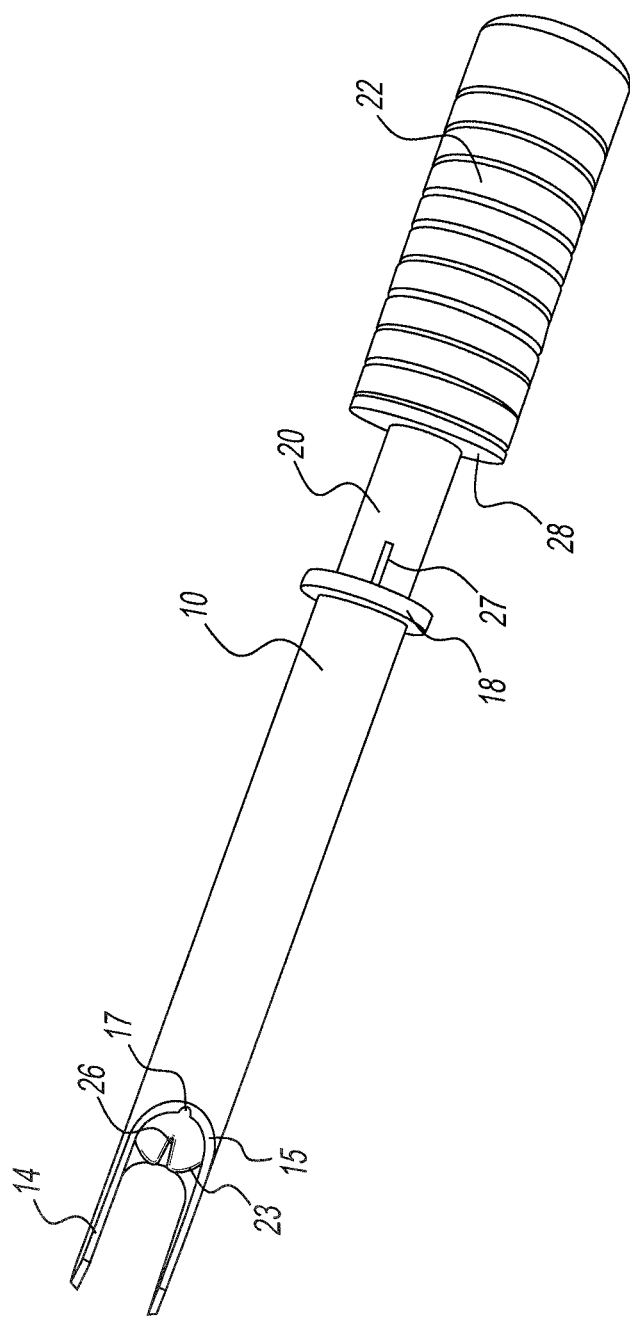
FIG. 11 shows the joint locator of FIG. 4 partially inserted into the working channel.
Figure 12:
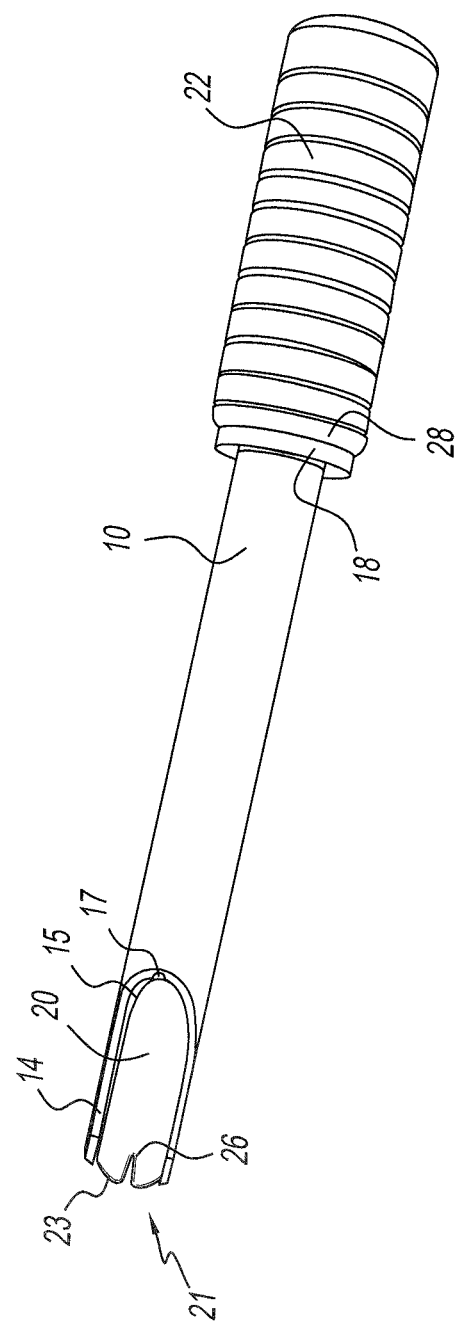
FIG. 12 shows the joint locator of FIG. 4 fully inserted into the working channel.

In one embodiment, referring to FIGS. 5, 11, and 12, the joint locator 20 has a channel 26 for receiving the K-wire 4. This channel 26 is a cannula, lumen, or other bore-like feature capable of receiving the K-wire 4 in a pass-through manner, preferably along a longitudinal axis, or centerline, of the joint locator 20. In one embodiment of the joint locator 20, the handle 22 further comprises a stop 28 for abutting against the channel collar 18 of the working channel 10.

Figure 13:
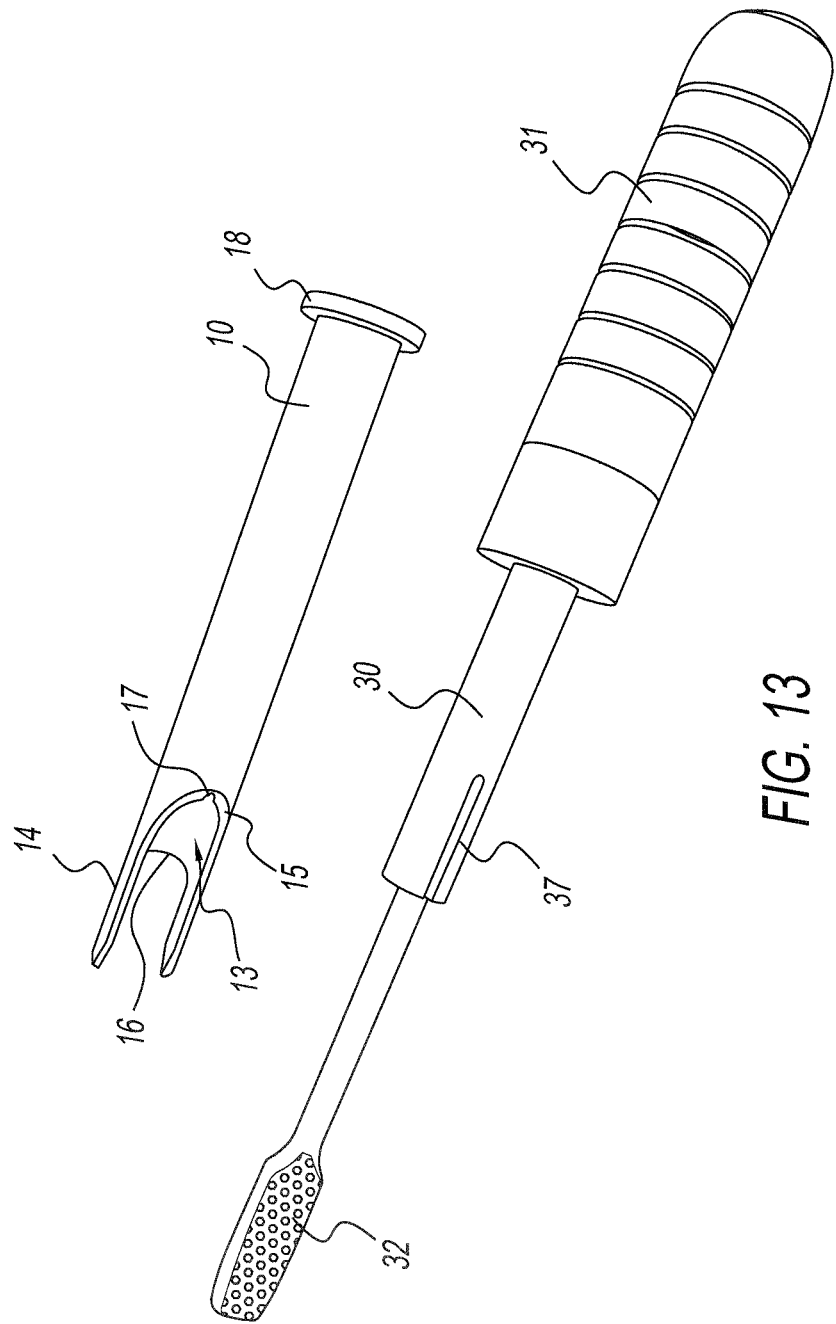
FIG. 13 shows the working channel of FIG. 4 and an embodiment of the abrading device.
Figure 15:
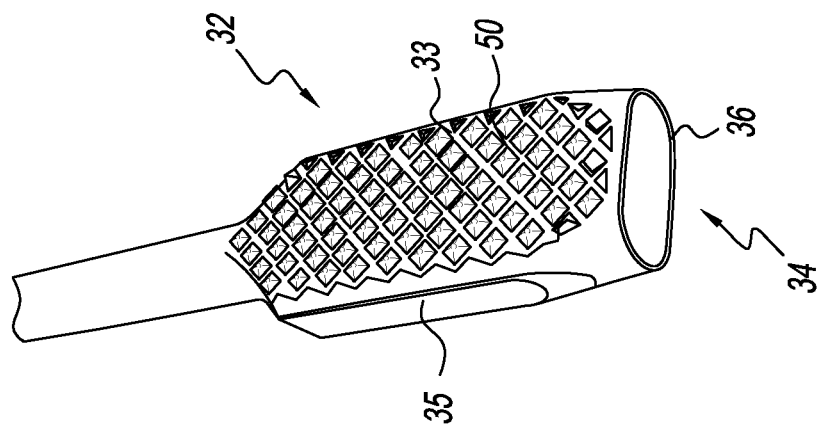
FIG. 15 shows an enlarged view of one embodiment of an abrading head.
Figure 14:
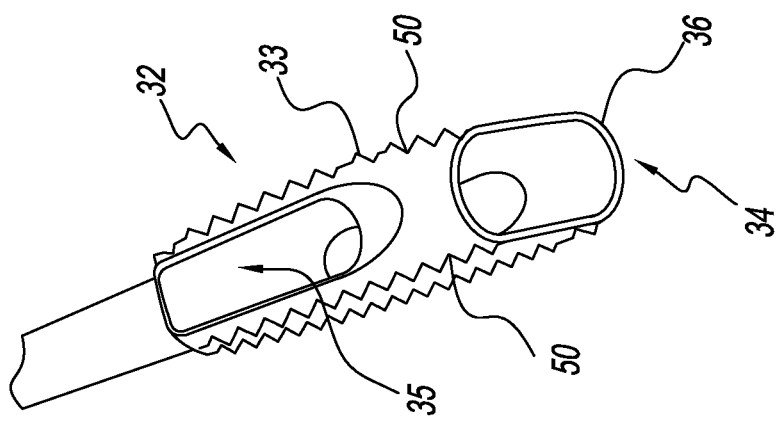
FIG. 14 is an enlarged view of an embodiment of the abrading head.

Referring to FIG. 13, the abrading device 30 comprises a hammer sleeve 31 at a proximal end and an abrading head 32 at a distal end. The abrading head 32 is a rasp, broach, or other abrading tool that is used to grate, abrade, or otherwise decorticate the cortical bone inside the SI Joint 3. In one embodiment, shown in FIGS. 14 and 15, the abrading head 32 is a generally rectangular member comprising abrading surfaces 33 on a first pair of opposing sides 50 of the head 32, an open tip 34 for insertion into the SI Joint 3, and a second pair of opposing sides 35 between the abrading surfaces 33, the second pair of opposing lateral sides 35 having one or more lateral openings. Each abrading surface 33 comprises one or more teeth, barbs, blades, ridges, slots, broaches, or other members or features capable of abrading the cortical bone in the SI Joint 3. The open tip 34 comprises a cutting edge 36 around all or part of the leading edge of the open tip 34, the cutting edge 36 configured for cutting bone tissue inside the SI Joint 3, such as the sacrum 1 or ilium 2. The abrading surfaces 33 and lateral sides 35 form a box-like abrading head 32 having a void therein. The openings in the lateral sides 35 enable lateral ingress into and egress from the void. For example, as the cutting edge 36 cuts bone tissue inside the SI Joint 3, the dislodged bone tissue falls into the void and may exit the abrading head 32 via the openings in the lateral sides 35.

In one embodiment, each side of the first pair of opposing sides 50 is a substantially planar member having a distal edge terminating at the open tip 34, the interface between the open tip 34 and the distal edge comprising a substantially straight cutting edge 36. Each side of the second pair of opposing sides 35 may comprise a curved distal portion terminating at the open tip 34, the interface between the open tip 34 and the curved distal portion comprising a curved cutting edge 36. The curved distal portion of each side of the second pair of opposing sides 35 may further comprise a taper toward its opposite side of the second pair of opposing sides 35.

Figure 19:
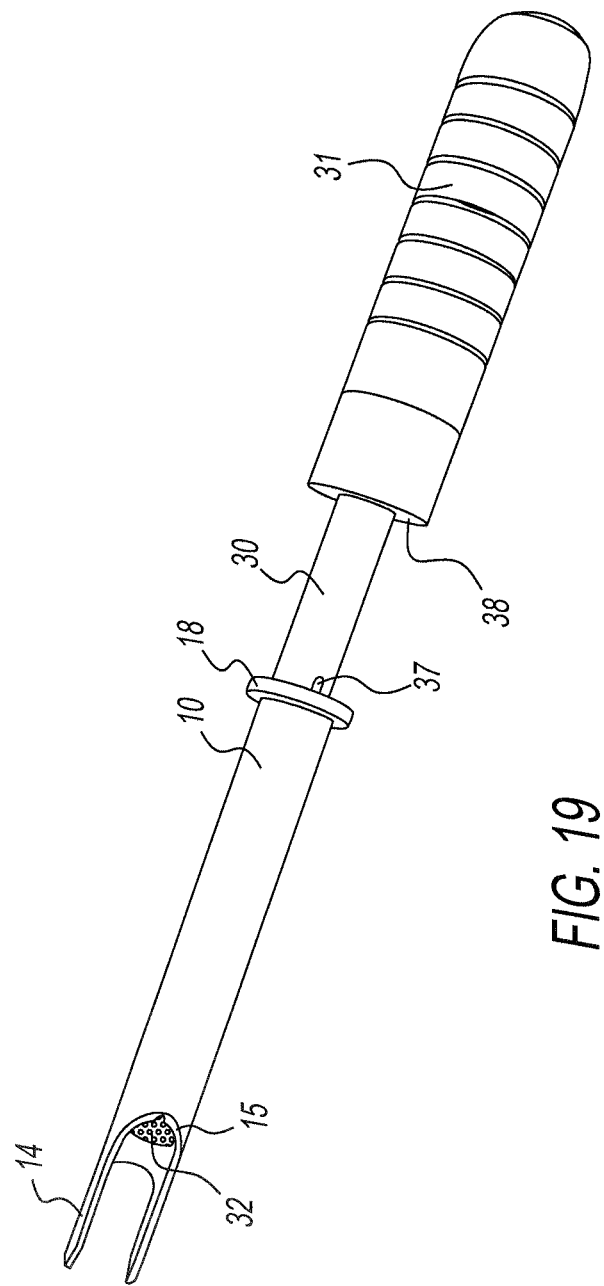
FIG. 19 shows the abrading device of FIG. 13 partially inserted into the working channel of FIG. 4.

Referring to FIG. 19, the abrading device 30 further comprises a keying means 37, which is similar to the joint locator 20 keying means 27 described above. The keying means 37 mates with the alignment means 17 in the working channel 10 to resist or to prevent relative rotation between the abrading device 30 and the working channel 10 about each member's respective longitudinal axis. The abrading device 30 further comprises an abrading stop 38 for abutting against the channel collar 18 of the working channel 10. In one embodiment, the abrading device 30 further comprises a K-wire channel for receiving the K-wire 4. This K-wire channel is a cannula, lumen, or other bore-like feature capable of receiving the K-wire 4 in a pass-through manner, preferably along a longitudinal axis of the abrading device 30.

Figure 17:
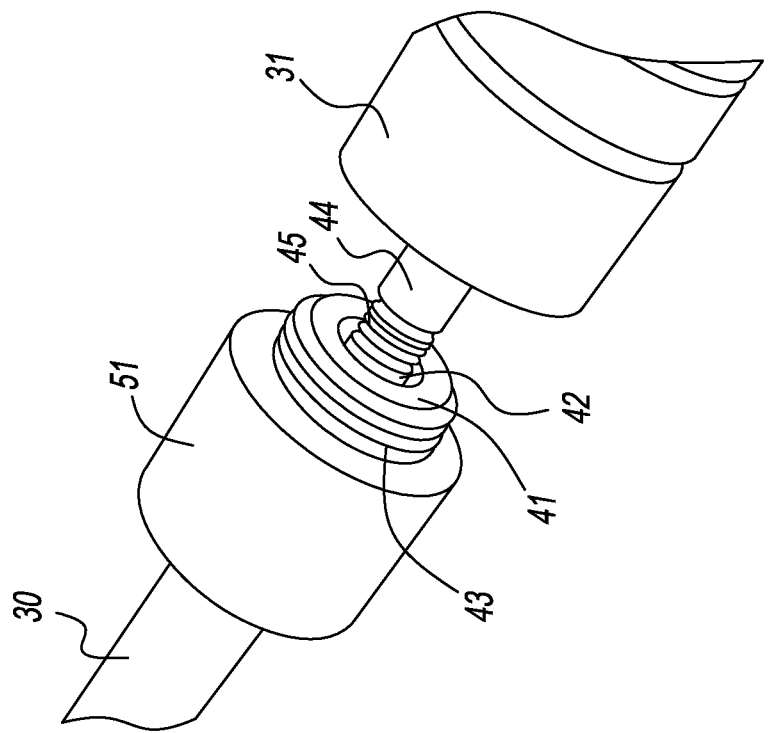
FIG. 17 is an enlarged view of an embodiment of the connection interface of a slide hammer.
Figure 16:
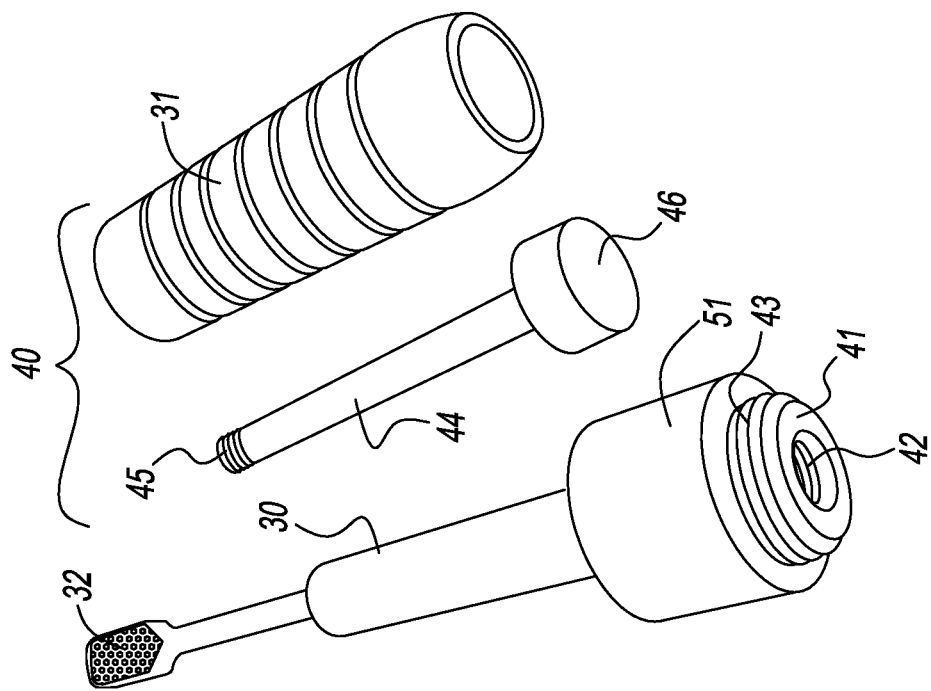
FIG. 16 shows the abrading device of FIG. 13 with an embodiment of a slide hammer disassembled.
Figure 18:
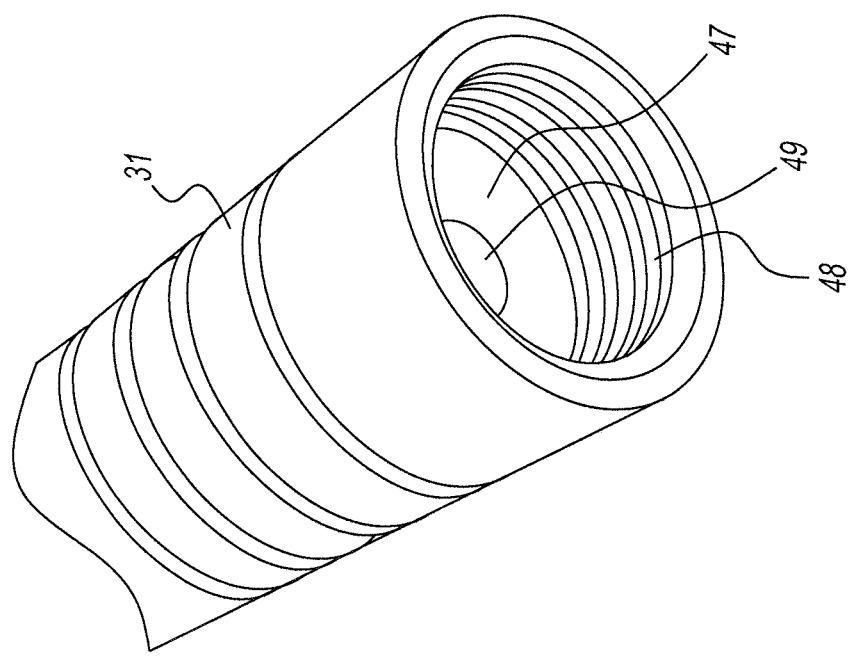
FIG. 18 shows a close up of one embodiment of the diaphragm and threaded connector of a slide hammer assembly.

Referring to FIGS. 16, 17, and 18, the abrading device 30 further comprises a slap hammer assembly, or slide hammer assembly 40. In one embodiment, the slide hammer assembly 40 comprises a base 51 connected to a shaft 44, and a releasing means that releasably connects a hammer sleeve 31 to the base 51. The released hammer sleeve 31 is configured for sliding engagement along the shaft 44. The releasing means is any means for releasably connecting the hammer sleeve 31 to the base 51, thereby transitioning the slide hammer assembly between its released position and its locked position. The releasing means could be a mating threaded connection, a quick disconnect attachment, a depressible tab, a latch, a clasp, a clip, a clamp, or other equivalent connection structure.

In one embodiment, shown in FIGS. 16, 17, and 18, the releasing means is a mating threaded connection. This embodiment includes a collar 41 on the abrading device 30, a slide hammer shaft 44, and the hammer sleeve 31. The collar 41 comprises internal threads 42 and external threads 43. The shaft 44 comprises a threaded end 45 and a stop end 46. The hammer sleeve 31 has a threaded connector 48 and a hollow, cylindrical bore comprising an internal diaphragm 47 having a diaphragm opening 49 (see FIG. 18). The diaphragm opening 49 is sized to permit sliding passage of all parts of the shaft 44 except the stop end 46. The stop end 46 is sized too large to fit through the diaphragm opening 49.

Figure 20:
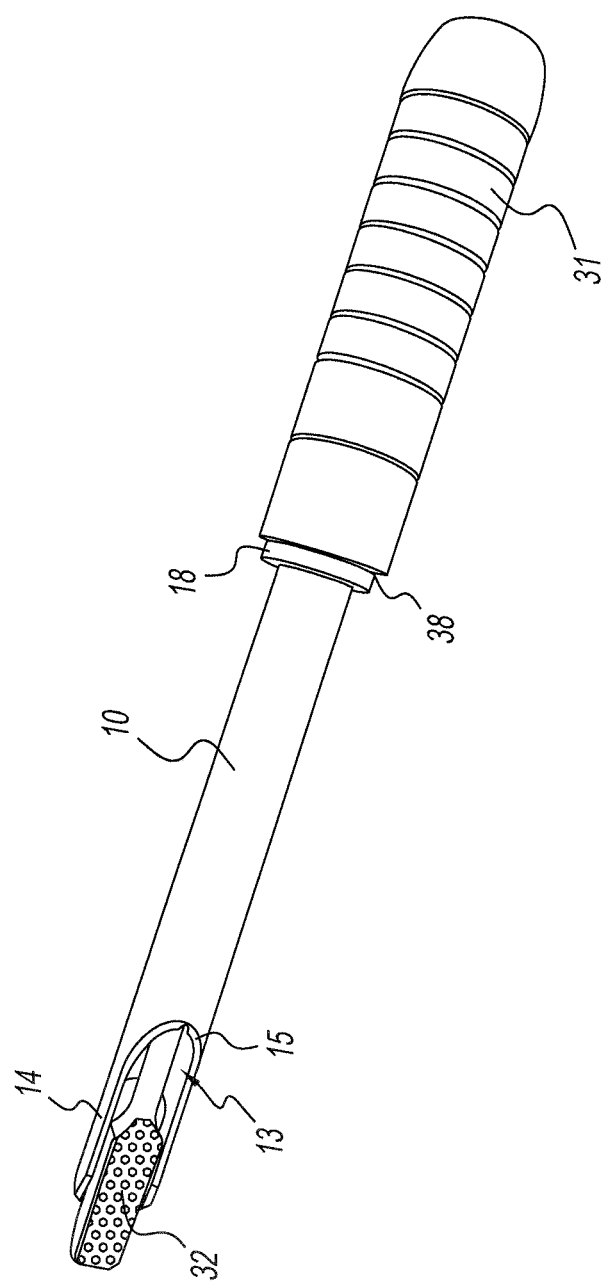
FIG. 20 shows the abrading device of FIG. 13 fully inserted into the working channel of FIG. 4 with the slide hammer in its locked position.

To assemble the slide hammer assembly 40 of this embodiment, the threaded end 45 of the shaft 44 is inserted into the bore of the hammer sleeve 31, through the diaphragm 47 inside the hammer sleeve 31, and the threaded end 45 is threaded into, and mated with, the internal threads 42 of the collar 41. The threaded connector 48 in the hammer sleeve 31 is then mated to the external threads 43 on the collar 41 to promote a secure connection. The stop end 46 is disposed inside the bore of the hammer sleeve 31 on a side of the diaphragm 47 opposite that of the location of the threaded connector 48. In this configuration, shown in FIG. 20, the slide hammer assembly 40 is in its locked position.

Figure 21:
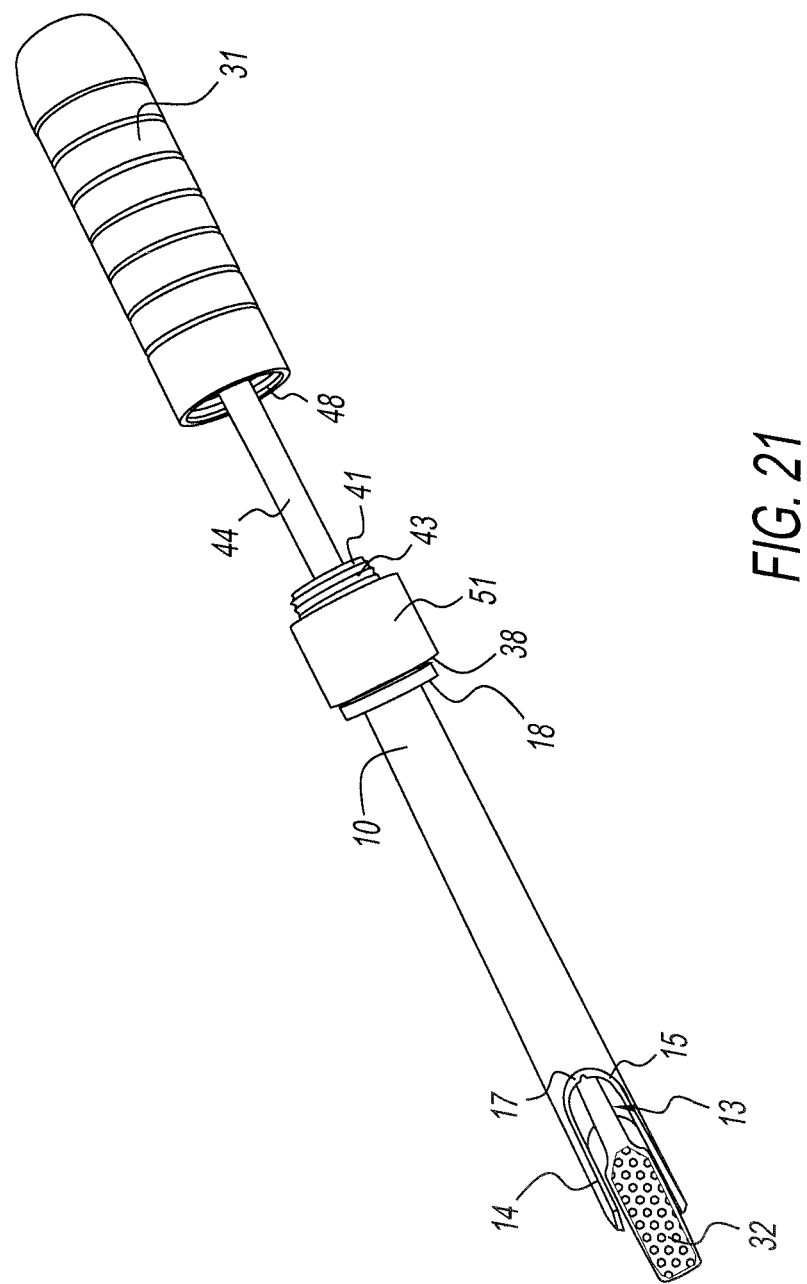
FIG. 21 shows the abrading device of FIG. 13 fully inserted into the working channel of FIG. 4 with the slide hammer in its extended position.
Figure 22:
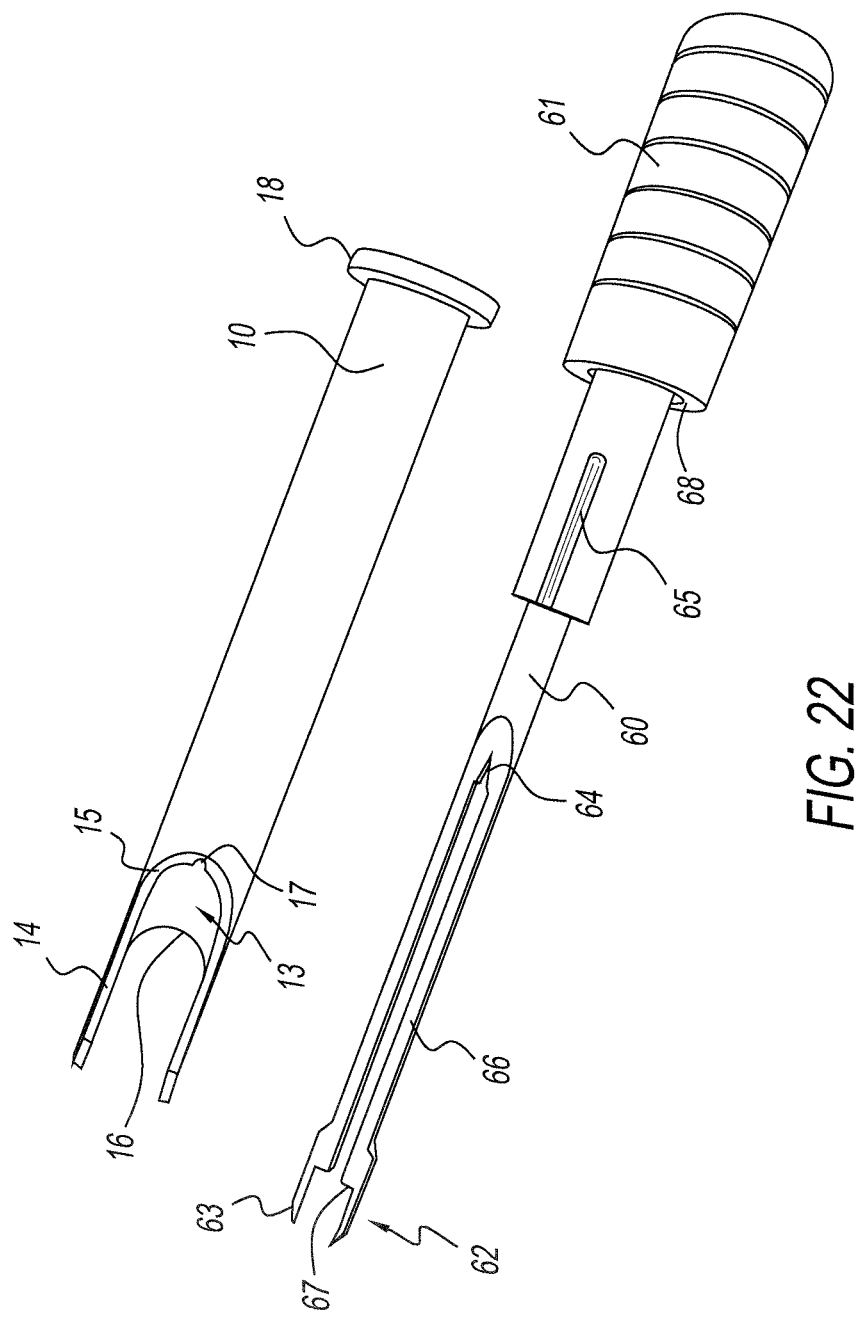
FIG. 22 shows the working channel of FIG. 4 and an embodiment of the insertion device.
Figure 23:
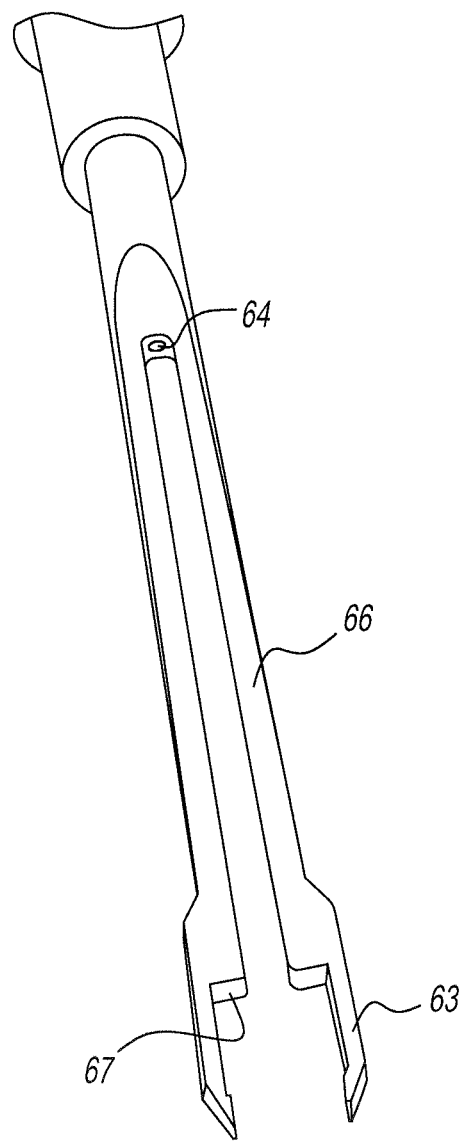
FIG. 23 is an enlarged view of the insertion end of the insertion device of FIG. 22.

To operate the slide hammer assembly 40, the threaded connector 48 is disengaged from the external threads 43 of the collar 41, placing the slide hammer assembly 40 in its released position, which is shown in FIG. 21. This released position enables the hammer sleeve 31 to slide freely along the shaft 44. The hammer sleeve 31 is pulled until the diaphragm 47 inside the hammer sleeve 31 engages the stop end 46 of the shaft 44, thereby causing an impact that delivers the slide hammer force. Thus, the slide hammer assembly has a released position that enables operation of the slide hammer assembly, and a locked position that prohibits operation of the slide hammer assembly.

Referring to FIGS. 22-26, the implant inserter 60 comprises a handle 61 and an implant insertion end 62. The implant insertion end 62 has a pair of tines 63 for holding the implant 5 during the process of inserting the implant 5 into the SI Joint 3. Each tine 63 is supported by a tine shaft 66, which terminates at a shoulder 67. The tine shafts 66 provide flexibility such that the implant 5 is removably retained between the tines 63 with the shoulder 67 abutting against the implant 5 (see FIG. 24). For example, in one embodiment the width of the implant 5 between the opposing grooves 8 is slightly larger than the space between the respective tines 63 such that when the implant 5 is seated in the implant insertion end 62, the respective tines 63 are pushed slightly apart by the grooves 8. This causes a slight amount of friction between the tines 63 and the grooves 8, thereby releasably retaining the implant 5 in the implant insertion end 62.

The implant inserter 60 further comprises an inserter keying means 65, which is similar to the keying means 27 of the joint locator 20. The inserter keying means 65 mates with the alignment means 17 in the working channel 10 to resist or to prevent relative rotation between the implant inserter 60 and the working channel 10 about each member's longitudinal axis. In one embodiment, the implant inserter 60 further comprises a channel 64 for receiving the K-wire 4 (see FIG. 23). This channel 64 is a cannula, lumen, or other bore-like feature capable of receiving the K-wire 4 in a pass-through manner. In one embodiment of the implant inserter 60, the handle 61 further comprises an inserter stop 68 for abutting against the channel collar 18 of the working channel 10.

In one embodiment of a method of installing the implant 5, the procedure for installing the implant 5 in the SI Joint 3 is started by locating an insertion point in the SI Joint 3, which is the location where the implant 5 is to be installed. For example, the free end of the K-wire 4 is inserted into the SI Joint 3 at the insertion point where the implant 5 is to be installed, thereby defining an intended location for the implant void. The implant void is a seat or groove between the sacrum 1 and ilium 2 for seating the implant 5, as described below. The K-wire 4 is preferably inserted from a posterior approach. It is preferable, but not required, that the implant 5 is installed under the portion of the posterior superior iliac spine that overhangs the SI Joint 3. One or more alternate location are also suitable for fusion of the SI Joint 3. A K-wire 4 is inserted into the SI Joint 3 at each location where an implant 5 is to be inserted.

In one embodiment, referring to FIGS. 27-31, the initial incision is made using an incision guide 70 that comprises a channel 71 for removably receiving a K-wire 4. The incision guide 70 further comprises a guide slot 72 for receiving a blade, scalpel, or similar cutting instrument (not shown). The guide slot 72 is disposed at an angle in relation to the channel 71 such that when the scalpel is extended through the guide slot 72, the tip of the scalpel is disposed above the patient's skin at the proper location for making the initial incision into the patient. This location is above the SI Joint 3 where the allograft implant 5 will be introduced into the soft tissue above the SI Joint 3, and eventually into the SI Joint 3 itself. In one embodiment, the guide slot 72 is oriented at an angle A of about 70° to about 75° in relation to horizontal H (see FIG. 30). In this orientation, the channel 71 is perpendicular to horizontal.

In this embodiment, the K-wire 4 is inserted into the SI Joint 3 as described above. The incision guide 70 is placed over the K-wire 4 such that the K-wire 4 is slidably received into the channel 71. In one embodiment, the scalpel is inserted into the guide slot 72 and retained in fixed relation to the channel 71 such that the cutting tip of the scalpel is located in close proximity to the K-wire 4. The incision guide 70 is then advanced toward the SI Joint 3, and the cutting tip of the scalpel makes the incision as the incision guide 70 advances. Once the initial incision is adequately formed, the incision guide 70 is lifted to remove it from the K-wire 4, and the surgery proceeds with other instruments for inserting the implant 5 into the SI Joint 3.

The joint locator 20 is then fully inserted into the working channel 10 (see FIG. 12). In mating the joint locator 20 inside the working channel 10, the keying means 27 of the joint locator 20 is oriented to engage the alignment means 17 of the working channel 10. This engagement enables the first iliac contour 15 of the working channel 10 to be disposed in mating alignment with the second iliac contour 24 of the joint locator 20, and the first sacral contour 16 of the working channel 10 to be disposed in mating alignment with the second sacral contour 25 of the joint locator 20 (see FIGS. 8 and 9). The respective first and second iliac contours 15, 24 are configured to be seated in mating placement against the ilium 2 when the insertion end 11 is disposed inside the SI Joint 3, and the respective first and second sacral contours 16, 25 are configured to be seated in corresponding mating placement against the sacrum 1 when the insertion end 11 is disposed inside the SI Joint 3. The stop 28 abuts against the channel collar 18 of the working channel 10 to prevent over penetration of the penetration tip 23 into the SI Joint 3, thereby avoiding damage to the soft tissue and nerves on the anterior side of the SI Joint 3.

The free end of the K-wire 4 is inserted into the K-wire channel 26 of the combined joint locator 20/working channel 10, and this combined device is advanced toward the SI Joint 3, guided by the K-wire 4. As the joint locator 20/working channel 10 combination is advanced, the penetration tip 23 cuts or tears though the soft tissue above and inside the SI Joint 3. If necessary, the combined joint locator 20/working channel 10 is advanced via blows from a mallet against the proximal end of the handle 22 to deliver an appropriate axial force. The impact from the mallet causes an axial force that is transmitted though the handle 22 to the stop 28, where the axial force is imparted to the channel collar 18 and into the working channel 10. As such, the impact force from a mallet is shared between the working channel insertion end 11 and the joint locator insertion end 21.

The combined joint locator 20/working channel 10 is advanced until the respective first and second iliac contours 15, 24 abut the ilium 2 and the respective first and second sacral contours 16, 25 abut the sacrum 1. In this position, the arms 14 of the working channel 10 are disposed inside the SI Joint 3 to retain the proper alignment of the working channel 10, and therefore the alignment means 17, thereby ensuring a proper alignment of the abrading device 30 and the implant inserter 60 later in the procedure. In some embodiments, insertion of the arms 14 into the SI joint 3 will distract the joint, thus separating the sacrum 1 and the ilium 2. This distraction establishes a uniform width of the spacing in the SI joint 3 prior to use of the other instrumentation. Thus, the instrumentation described herein will work with a patient of any size because the arms 14 set the width of the SI joint 3 to a uniform distance regardless of the size or scale of the sacrum 1 or ilium 2.

In an alternate embodiment of the installation method, a K-wire 4 is omitted from the procedure. Instead, the combined joint locator 20/working channel 10 is advanced through an incision in the patient, and this advancement continues as described above until the insertion ends 11, 21 are inserted into the SI Joint 3 as described above.

Once the combined joint locator 20/working channel 10 device is properly seated in the SI Joint 3, the joint locator 20 is removed from the working channel 10. The surrounding soft tissue remains distracted or dilated by the working channel 10 and the respective arms 14, thereby enabling direct access to the SI Joint 3 area. The abrading device 30 is then inserted into the working channel 10, with the keying means 37 engaging the alignment means 17 to promote proper alignment of the abrading head 32 with respect to the SI Joint 3. The abrading head 32 is advanced through the working channel 10 until the abrading head 32 makes contact with the SI Joint 3. The abrading head 32 is forced into the SI Joint 3 (using a mallet if necessary), and the cutting edge 36 cuts the bone tissue and any soft tissue, such as ligaments or cartilage. The abrading stop 38 abuts against the channel collar 18 of the working channel 10 to prevent over penetration of the abrading head 32 into the SI Joint 3, thereby avoiding damage to the soft tissue and nerves on the anterior side of the SI Joint 3. During this process, the cutting edge 36 cuts through the relevant bone portions of the sacrum 1 and ilium 2, and the abrading surfaces 33 works in connection with the cutting edge 36 to decorticate the cortical bone inside the SI Joint 3, thereby forming a decorticated implant void at the insertion point of the SI Joint 3. The decorticated implant void has a generally rectangular cross sectional shape such that the decorticated implant void is adapted for receiving the fusion implant 5, which has a generally rectangular cross sectional shape for mating with the decorticated implant void. Thus, use of the abrading head 32 enables installation of the implant 5 without the need for using a drill or other rotary cutting instrument to form a pilot hole for the implant 5. As used herein, a rotary cutting instrument is any device capable of cutting material by turning, rotating, or other angular motion about an axis of the device, whether power-driven or hand-driven. This is a significant improvement of the present set of instruments over prior art methods and instrument sets for SI Joint 3 fusion.

The abrading device 30 is then worked in and out of the working channel 10 such that the abrading surfaces 33 abrade, or decorticate, the respective surfaces of the sacrum 1 and the ilium 2 inside the SI Joint 3. Again, the abrading stop 38 abuts against the channel collar 18 to prevent over penetration of the abrading head 32. During this process, the abrading head 32 may become lodged in the SI Joint 3, becoming difficult to remove. In these instances, the slide hammer assembly 40 is enabled so that the abrading head 32 may be removed by the impact force of the slide hammer assembly 40, as described above. Operation of the slide hammer assembly 40 provides a significant advantage over prior systems because when the abrading head 32 becomes lodged in the SI joint 3, counter pressure cannot be applied to the patient to counter the pull-out force needed to dislodge the abrading head 32 from the SI joint 3. The slide hammer assembly 40 enables removal of a lodged abrading head 32 in a safe manner without applying any counter pressure to the patient.

As the abrading head 32 is worked in and out of the SI Joint 3, the abrading surfaces 33 abrade the cortical bone of the sacrum 1 and the ilium 2 inside the SI Joint 3. The cortical bone is abraded until bleeding begins, thereby promoting the patient's healing process of the cortical bone. This degree of abrasion and corresponding healing promotes fusion of the SI Joint 3.

Once the SI Joint 3 is adequately abraded, the abrading device 30 is removed from the working channel 10. Thus, this method of fusing the SI Joint 3 comprises steps for forming a void for a fusion implant 5 in the SI Joint 3 without using a rotary cutting instrument. At this point in the procedure, the K-wire 4 may be removed from the working channel 10 to enable proper advancement of the implant 5 through the working channel 10 and proper installation of the implant 5 into the SI Joint 3. Alternately, the K-wire 4 can be removed from the working channel 10 at any time after the working channel 10 is properly seated in the SI Joint 3, as described above.

Figure 24:
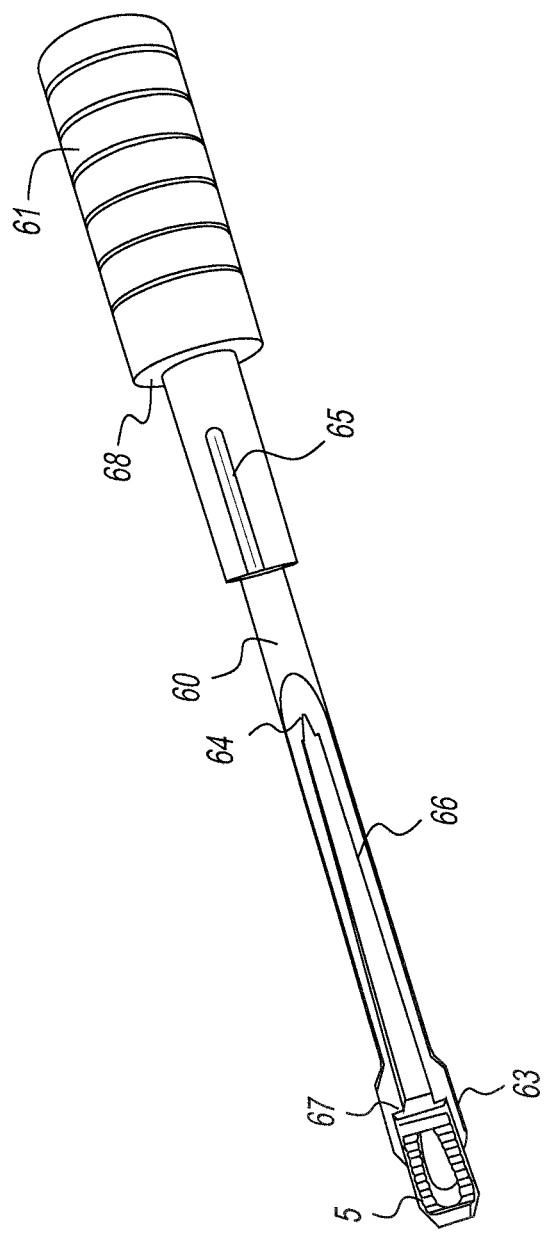
FIG. 24 shows the insertion device of FIG. 22 with an embodiment of an allograft implant loaded into the tines of the insertion end.
Figure 25:
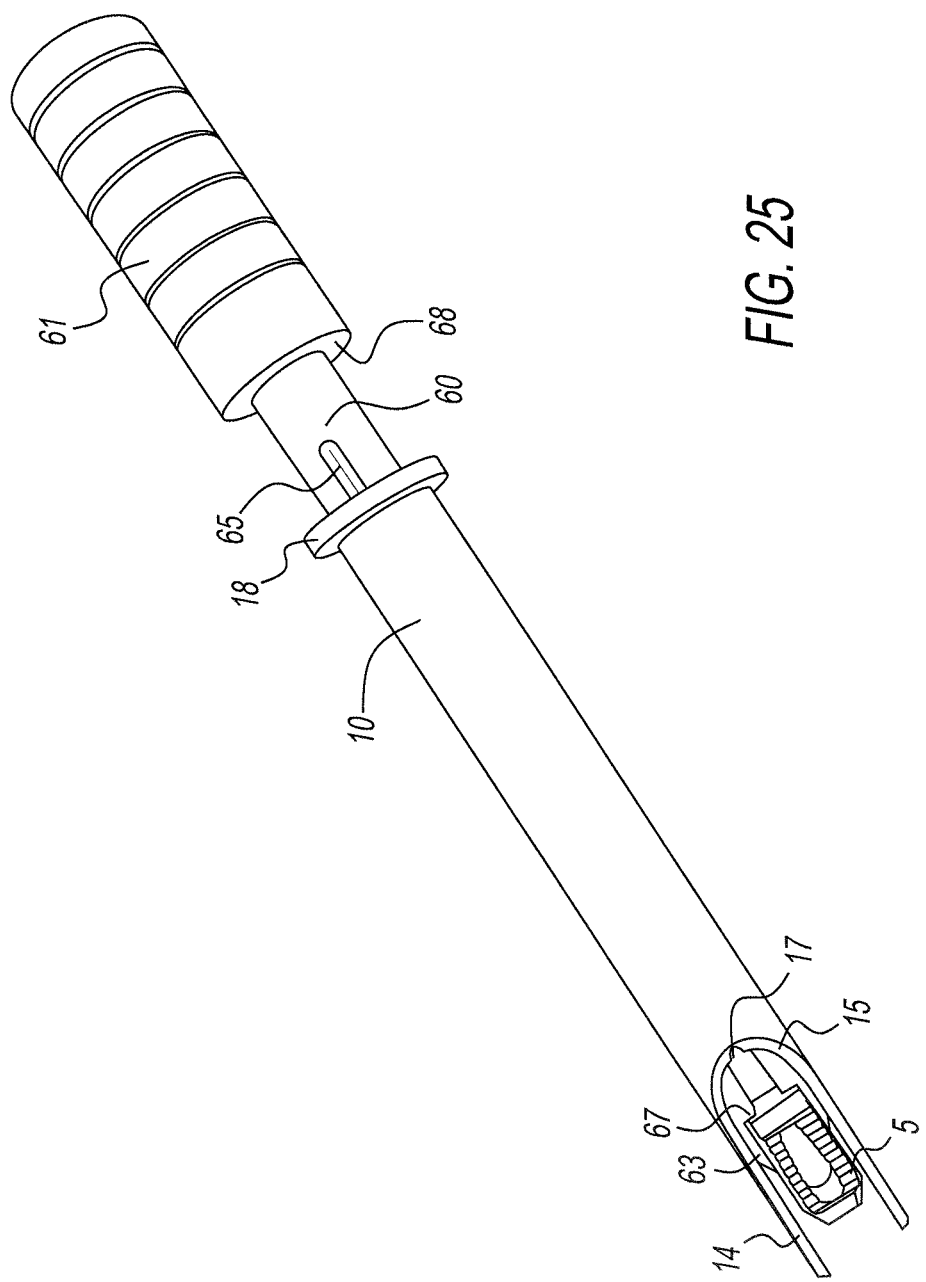
FIG. 25 shows the insertion device of FIG. 22 and the allograft implant partially inserted into the working channel of FIG. 4.
Figure 26:
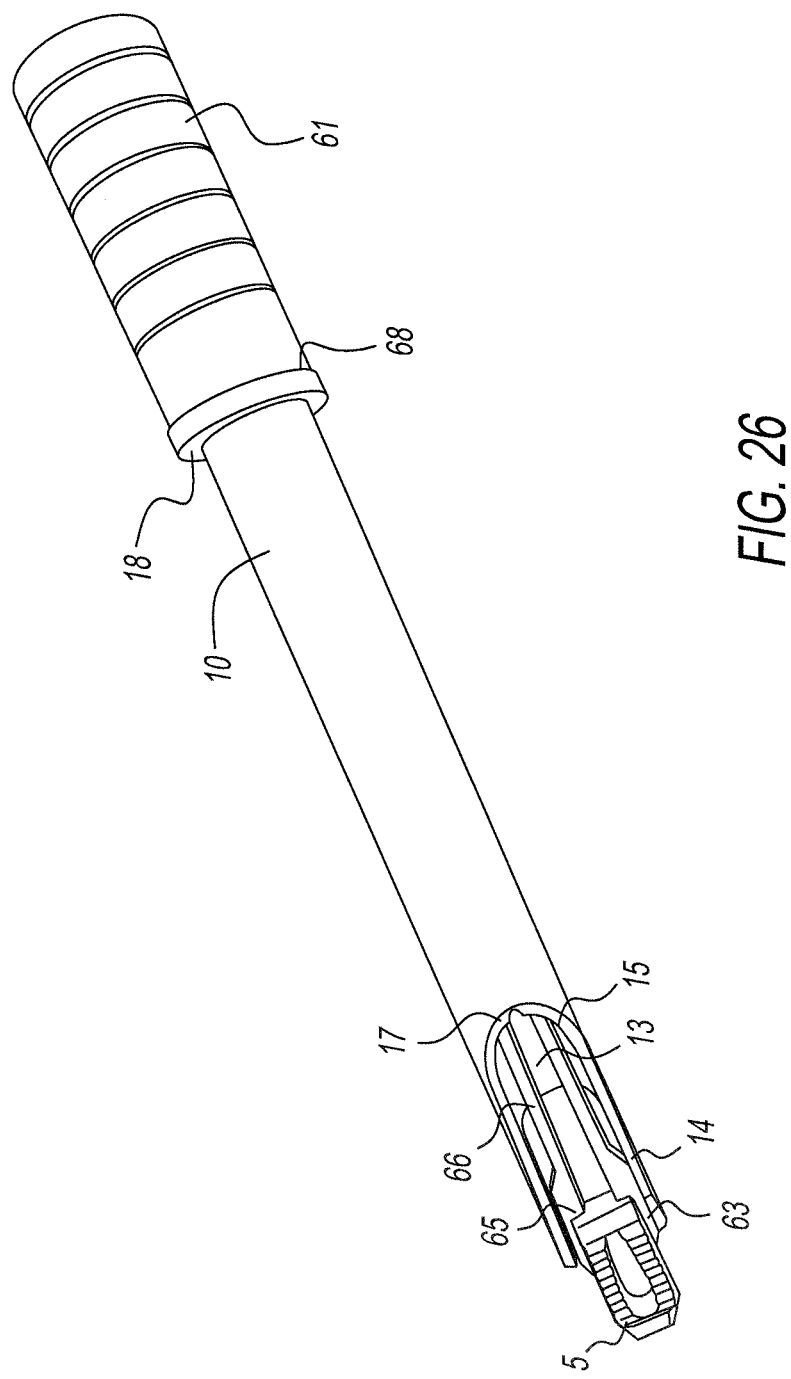
FIG. 26 shows the insertion device of FIG. 22 and the allograft implant fully inserted into the working channel of FIG. 4.
Figure 27:
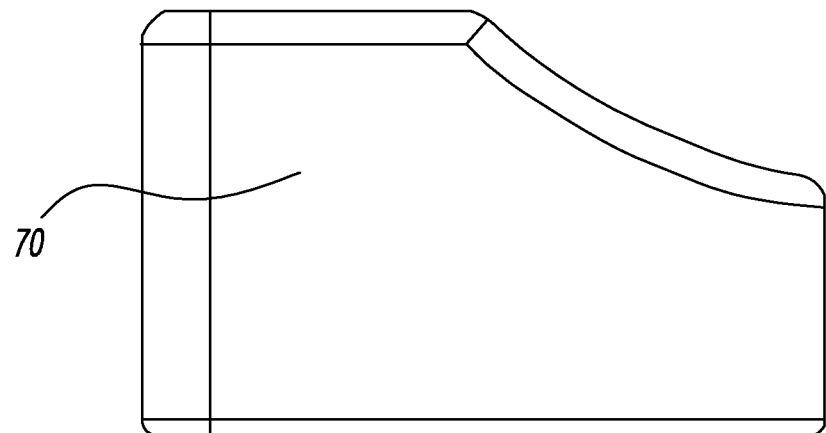
FIG. 27 is a front view of one embodiment of the incision guide.
Figure 28:
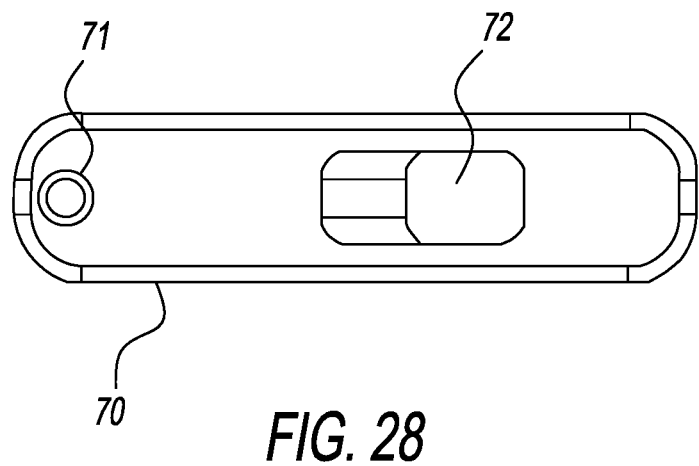
FIG. 28 is a top view of one embodiment of the incision guide
Figure 29:
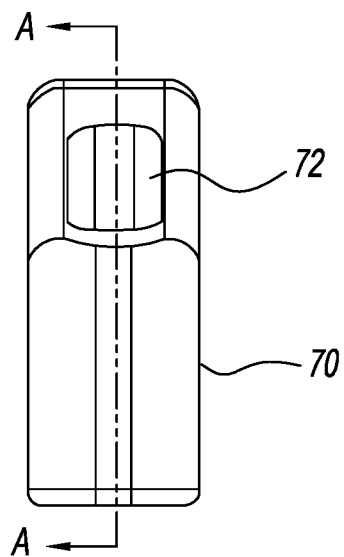
FIG. 29 is a right side view of one embodiment of the incision guide.
Figure 30:
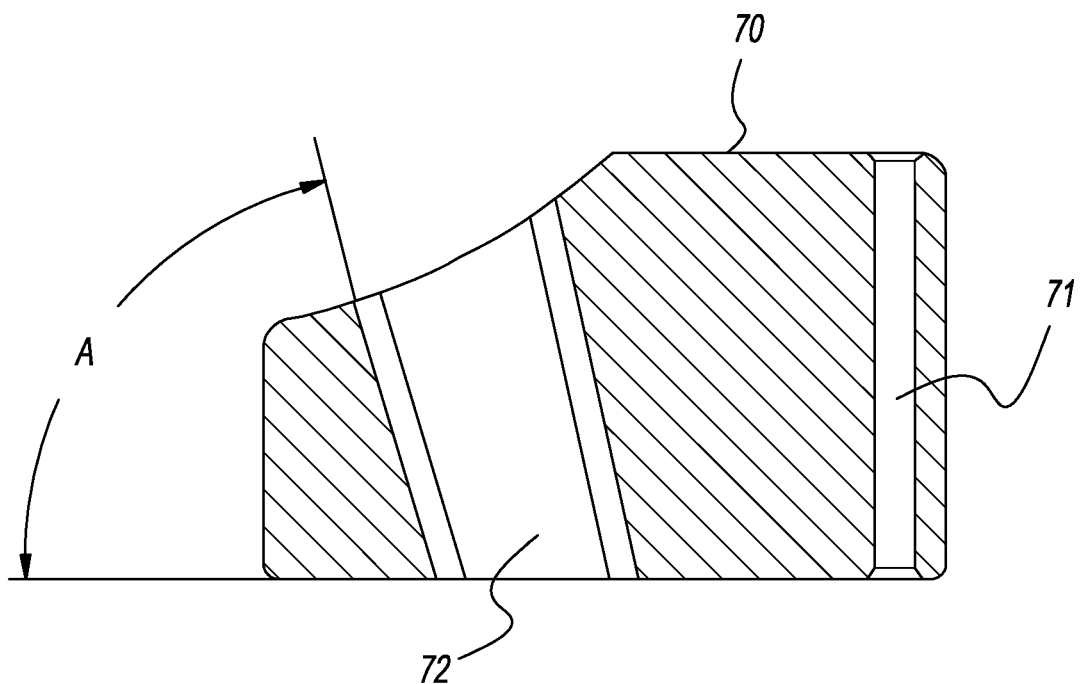
FIG. 30 is a cross-sectional view A-A of the incision guide of FIG. 29.
Figure 31:
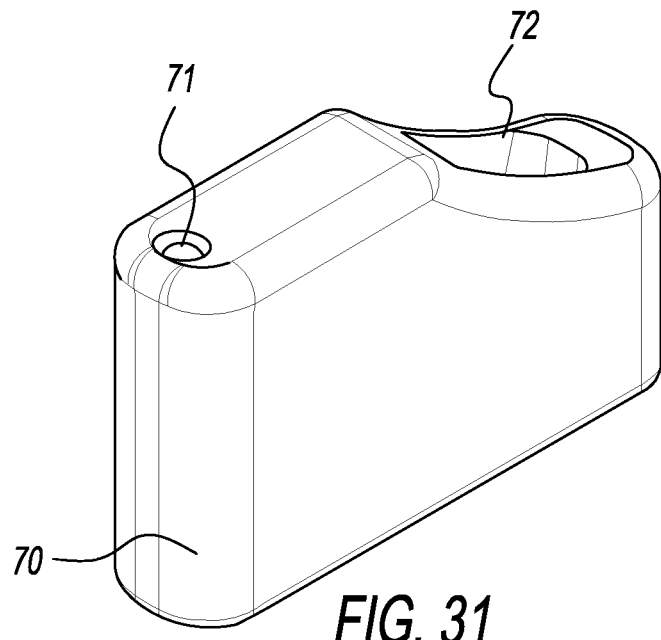
FIG. 31 is an isometric view of one embodiment of the incision guide.
Figure 32:
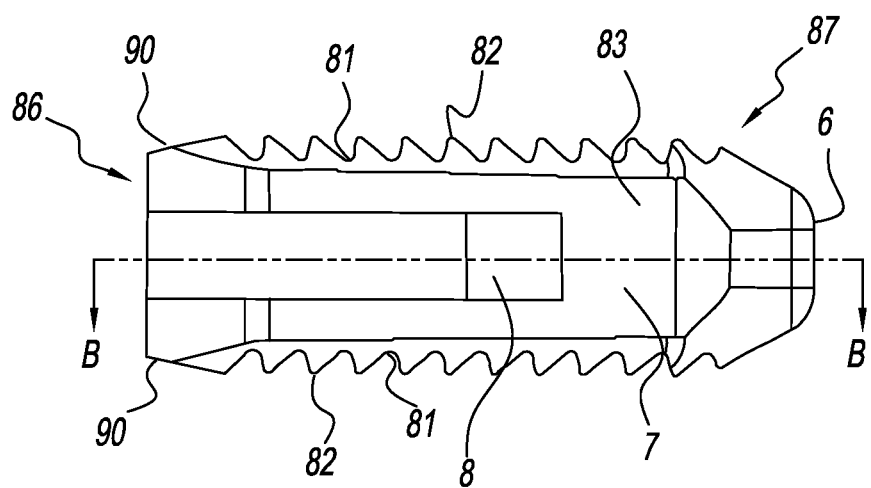
FIG. 32 is a side view of one embodiment of an allograft implant.

The allograft implant 5 is placed into the tines 63 of the implant inserter 60 such that each tine 63 is seated into a mating groove 8 on the lateral side 7 of the implant 5, and the shoulder 67 abuts the implant 5 (see FIG. 24). The implant inserter 60 is then inserted into the working channel 10 such that the keying means 65 engages the alignment means 17 to ensure proper orientation of the implant inserter 60, and thus, the implant 5. The implant inserter 60 is used to deliver the implant 5 to the abraded area of the SI Joint 3 through the working channel 10. If necessary, the implant inserter 60 is struck by a mallet to force the implant 5 into the abraded area of the SI Joint 3, the shoulder 67 transferring the impact force to the implant 5. In these instances, the inserter stop 68 abuts against the channel collar 18 of the working channel 10 to prevent over penetration of the implant 5 into the SI Joint 3, thereby ensuring that the implant 5 is properly placed inside the SI Joint 3.

Once the implant 5 is fully inserted into the SI Joint 3, the implant inserter 60 is removed from the working channel 10, leaving the implant 5 installed in the abraded area of the SI Joint 3. In most instances, the friction force between the implant 5 and the inside of the SI Joint 3 is greater than the friction force between the respective tines 63 and grooves 8. In these instances, removal of the implant inserter 60 is accomplished by applying a removal force to the implant inserter 60 greater than the friction force between the tines 63 and the grooves 8. The tines 63 slide out of the grooves 8 as the implant inserter 60 is retracted from the working channel 10. In other instances, the friction force between the implant 5 and the inside of the SI Joint 3 is less than the friction force between the respective tines 63 and grooves 8. In these instances, removal of the implant inserter 60 is accomplished by inserting a K-wire 4 or similar device into the K-wire channel 64 and advancing the K-wire 4 until the distal end of the K-wire 4 abuts against the implant 5 between the tines 63. The K-wire 4 is used to hold the implant 5 in place inside the SI Joint 3 as the removal force is applied to the implant inserter 60. The tines 63 are thereby removed from the grooves 8 as the K-wire 4 holds the implant 5 in its installed location. Once the tines 63 are pulled free from the grooves 8, the implant inserter 60 is disengaged from the implant 5, and the implant inserter 60 and the K-wire 4 are removed from the working channel 10. The working channel 10 is then removed from the surgical site, causing the SI Joint 3 to contract, thereby exerting a compressive force on the implant 5. This compressive force is caused by the ligaments of the SI Joint 3 that compress the joint, thereby holding it together. The surgical site is then sterilized and closed for healing.

As the abraded cortical bone heals, the bone fuses with the allograft implant 5, eventually causing the sacrum 1 and the ilium 2 to grow together at the location of the implant 5, thereby fusing the SI Joint 3.

In any of the foregoing embodiments, one or more instruments may comprise disposable material, such as medical grade plastics, certain metals, or other disposable material.

Referring to FIGS. 32-36, the implant 5 generally has two opposing faces 81. When the implant 5 is inserted into the SI Joint 3, one opposing face 81 is disposed against the sacrum 1, and the other opposing face 81 is disposed against the ilium 2. Each of the opposing faces 81 comprises one or more anti-migration features 82, such as teeth or ridges, that resist movement of the implant inside the SI Joint 3.

In one embodiment, the implant 5 comprises a body 83 having a proximal end 86, a distal end 87, and a length disposed therebetween, the distal end having a rounded nose 6. The body 83 further comprises two sides 7, each side 7 comprising a groove 8 beginning at the proximal end 86 of the body 83 and continuing along each of the two sides 7 for at least part of the length, the distance between the two sides 7 defining a width W of the body.

The implant 5 further comprises a central graft window 85 that enables fusion of the SI Joint 3 to occur through the implant 5. The graft window 85 is disposed between each of the opposing faces 81, the graft window 85 providing passage through the body 83 between the two opposing faces 81. The portion of the body 83 located between the graft window 85 and each of the sides 7 defines a wall 84.

Figure 33:
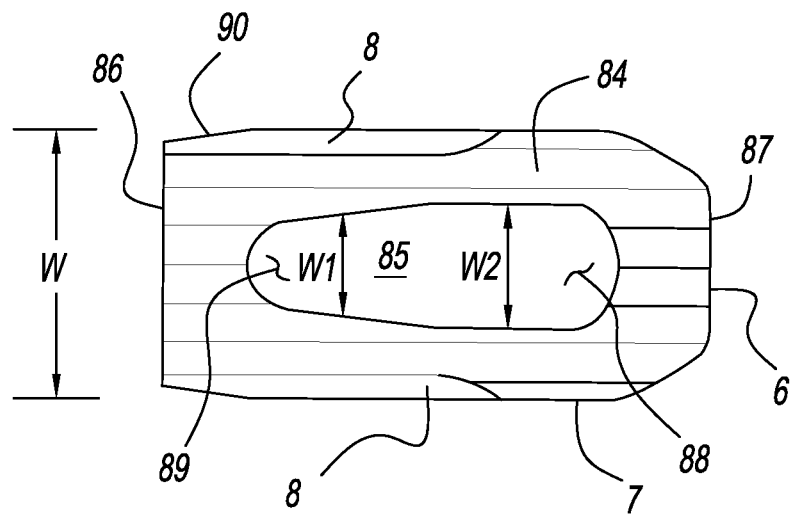
FIG. 33 is a cross-sectional view B-B of the allograft implant of FIG. 32.
Figure 34:
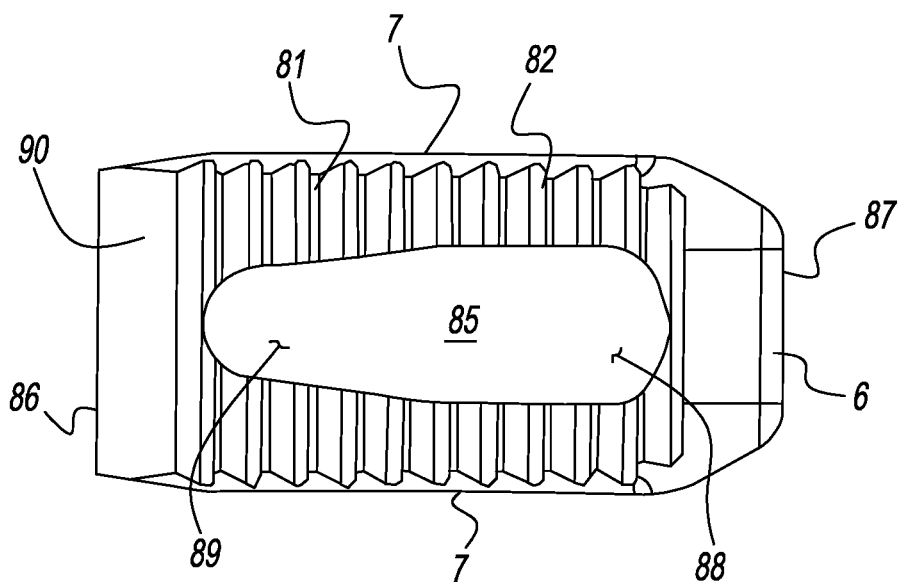
FIG. 34 is a top view of one embodiment of an allograft implant.
Figure 35:
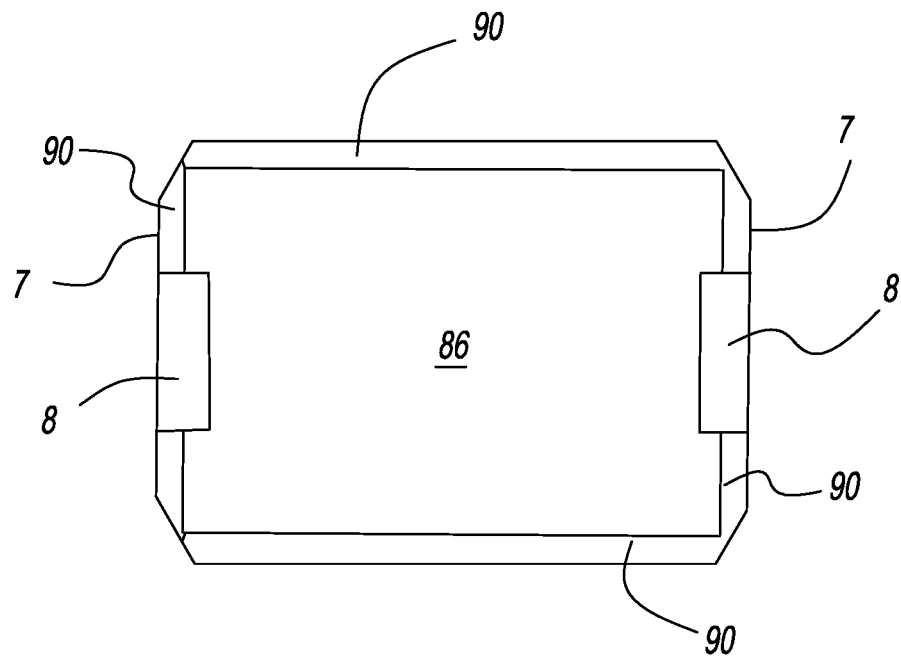
FIG. 35 is a rear view of one embodiment of an allograft implant.
Figure 36:
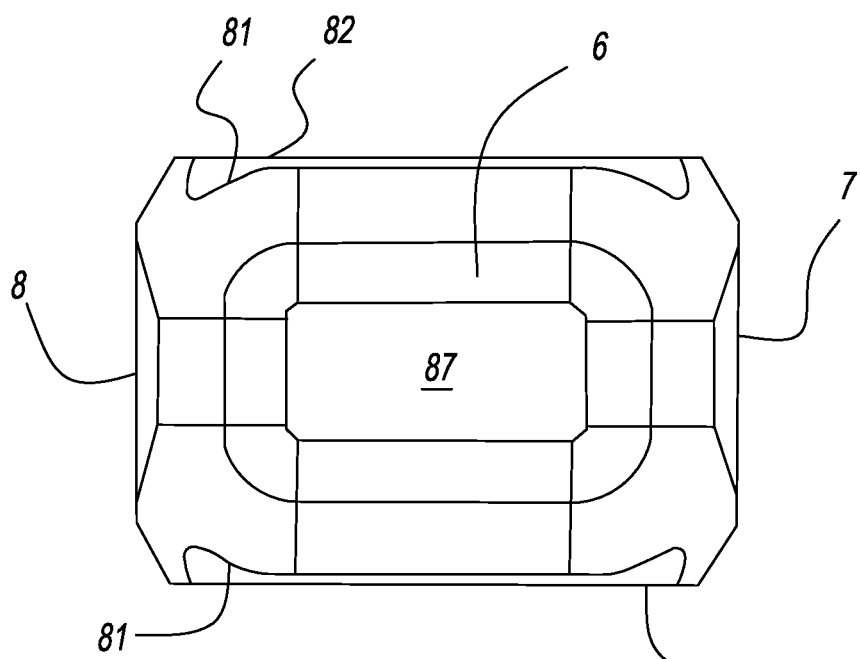
FIG. 36 is a front view of one embodiment of an allograft implant.

When viewed in cross section (see FIG. 33), the area of the graft window 85 is about 35% to about 40% of a first cross-sectional area of the body, which is the area of the total implant 5 as shown by the hatched area in FIG. 33. The area of the window 85 is about 60% of the total area of each opposing face 81 that makes contact with the bone, whether the sacrum 1 or the ilium 2. These ratios provide a strength-to-contact area relationship that optimizes performance of the implant 5 as a promoter of SI Joint 3 fusion. In these ratios, the implant 5 provides enough strength so that it is not crushed inside the SI Joint 3, and it provides a large enough graft window 85 to expedite fusion of the SI Joint 3 across and through the implant 5.

In one embodiment, the graft window 85 has a proximal portion 88 located in proximity to the grooves 8, and a distal portion 89, the proximal portion 88 having a width W1 that is less than a width W2 of the distal portion 89 such that the wall 84 maintains a minimum thickness in a range of about 17% to about 20% of the width W of the body 83.

In the foregoing embodiments, it is preferable, but not required, that the graft window 85 is unobstructed by internal or intermediate supports. Such internal or intermediate supports are sometimes used in allograft implants to provide structural support to the implant. However, these internal or intermediate supports obstruct bone fusion from occurring through the window. As such, the graft window 85 may provide an open passage through the body 83 between the opposing faces 81. The open passage may be rectilinear or curvilinear. The proximal end 86 of the body 83 may further comprise a taper 90 that reduces a second cross-sectional area of the body 83.

The foregoing embodiments are merely representative of the SI Joint fusion instruments and multimodal abrading device, and these embodiments are not meant for limitation of the invention. For example, persons skilled in the art would readily appreciate that there are several embodiments and configurations of slide hammer devices, abrading surfaces, and other features described herein that will not substantially alter the nature of the SI Joint fusion instruments and abrading device. As another example, the alignment means 17 and the respective keying means 27, 37, 67 could be reversed such that the working channel 10 comprises a keying means, and the joint locator 20, rasp device 30, and implant inserter 60, respectively, comprise a mating alignment means. Consequently, it is understood that equivalents and substitutions for certain elements and components set forth above are part of the invention described herein, and the true scope of the invention is set forth in the claims below.

What is claimed is:

1. A multimodal abrading device for forming a fusion implant insertion location in a sacroiliac joint, the abrading device comprising:
an abrading head at a distal end of the abrading device, the abrading head having:
abrading surfaces on each of a first pair of opposing sides, the abrading surfaces comprising one or more teeth, barbs, blades, ridges, slots, broaches, or other members capable of abrading a cortical bone of the sacroiliac joint;
an open tip comprising a cutting edge disposed at a leading edge of the open tip, the cutting edge configured to cut bone tissue in the sacroiliac joint; and
a void and a second pair of opposing sides, each side of the second pair of opposing sides comprising a curved distal portion terminating at the open tip, an interface between the open tip and the curved distal portion comprising a curved cutting edge; and a slide hammer assembly at a proximal end of the abrading device, the slide hammer assembly having a released position that enables operation of the slide hammer assembly, and a locked position that prohibits operation of the slide hammer assembly.

2. The multimodal abrading device of claim 1, wherein, each of the second pair of opposing sides has an opening for enabling lateral ingress into and egress from the void.

3. The multimodal abrading device of claim 1, wherein each side of the first pair of opposing sides is a substantially planar member having a distal edge terminating at the open tip, an interface between the open tip and the distal edge comprising a substantially straight cutting edge.

4. The multimodal abrading device of claim 2, wherein each side of the first pair of opposing sides is a substantially planar member having a distal edge terminating at the open tip, an interface between the open tip and the distal edge comprising a substantially straight cutting edge.

5. The multimodal abrading device of claim 4, wherein the curved distal portion of each side of the second pair of opposing sides comprises a taper toward its opposite side of the second pair.

6. The multimodal abrading device of claim 1, wherein the curved distal portion of each side of the second pair of opposing sides comprises a taper toward its opposite side of the second pair.

7. The multimodal abrading device of claim 6, wherein each side of the first pair of opposing sides is a substantially planar member having a distal edge terminating at the open tip, the interface between the open tip and the distal edge comprising a substantially straight cutting edge.

8. A multimodal abrading device for forming a fusion implant insertion location in a sacroiliac joint, the abrading device comprising:

an abrading head at a distal end of the abrading device, the abrading head having:
abrading surfaces on each of a first pair of opposing sides, the abrading surfaces comprising one or more teeth, barbs, blades, ridges, slots, broaches, or other members capable of abrading a cortical bone of the sacroiliac joint;
an open tip comprising a cutting edge disposed at a leading edge of the open tip, the cutting edge configured to cut bone tissue in the sacroiliac joint; and
a void and a second pair of opposing sides, each side of the second pair of opposing sides comprising a curved distal portion terminating at the open tip, the interface between the open tip and the curved distal portion comprising a curved cutting edge; and a slide hammer assembly at a proximal end of the abrading device, the slide hammer assembly having a released position that enables operation of the slide hammer assembly, a locked position that prohibits operation of the slide hammer assembly, and a releasing means for transitioning the slide hammer assembly between the locked position and the released position.

9. The multimodal abrading device of claim 8, wherein each side of the first pair of opposing sides is a substantially planar member having a distal edge terminating at the open tip, an interface between the open tip and the distal edge comprising a substantially straight cutting edge.

10. The multimodal abrading device of claim 8, wherein each of the second pair of opposing sides has an opening for enabling lateral ingress into and egress from the void.

11. The multimodal abrading device of claim 8, wherein the curved distal portion of each side of the second pair of opposing sides comprises a taper toward its opposite side of the second pair.

12. A multimodal abrading device for forming a fusion implant insertion location in a sacroiliac joint, the abrading device comprising:

an abrading head at a distal end of the abrading device, the abrading head having:
abrading surfaces on each of a first pair of opposing sides, the abrading surfaces comprising one or more teeth, barbs, blades, ridges, slots, broaches, or other members capable of abrading a cortical bone of the sacroiliac joint; and
an open tip comprising a cutting edge disposed at a leading edge of the open tip, the cutting edge configured to cut bone tissue in the sacroiliac joint; and a slide hammer assembly at a proximal end of the abrading device, the slide hammer assembly having a released position that enables operation of the slide hammer assembly, a locked position that prohibits operation of the slide hammer assembly, and a releasing means for transitioning the slide hammer assembly between the locked position and the released position;

a collar on the abrading device, the collar having internal threads and external threads;

a slide hammer shaft having a threaded end for mating with the internal threads of the collar on the abrading device, and having a slide stop end opposite from the threaded end; and a hammer sleeve having a hollow, cylindrical bore comprising an internal diaphragm and a threaded connector configured for mating with the external threads of the collar such that when mated the hammer sleeve is engaged in the locked position, the diaphragm having a diaphragm opening sized to permit sliding passage of the slide hammer shaft and block passage of the slide stop end.

13. The multimodal abrading device of claim 12, wherein the abrading head further comprises a void and a second pair of opposing sides, each of the second pair of opposing sides having an opening for enabling lateral ingress into and egress from the void.

14. The multimodal abrading device of claim 12, wherein each side of the first pair of opposing sides is a substantially planar member having a distal edge terminating at the open tip, an interface between the open tip and the distal edge comprising a substantially straight cutting edge.

15. The multimodal abrading device of claim 12, wherein the abrading head further comprises a void and a second pair of opposing sides, each side of the second pair of opposing sides comprising a curved distal portion terminating at the open tip, an interface between the open tip and the curved distal portion comprising a curved cutting edge.

16. The multimodal abrading device of claim 13, wherein each side of the first pair of opposing sides is a substantially planar member having a distal edge terminating at the open tip, an interface between the open tip and the distal edge comprising a substantially straight cutting edge.

17. The multimodal abrading device of claim 16, wherein each side of the second pair of opposing sides comprises a curved distal portion terminating at the open tip, the interface between the open tip and the curved distal portion comprising a curved cutting edge.

18. The multimodal abrading device of claim 15, wherein the curved distal portion of each side of the second pair of opposing sides comprises a taper toward its opposite side of the second pair.

19. The multimodal abrading device of claim 18, wherein each side of the first pair of opposing sides is a substantially planar member having a distal edge terminating at the open tip, an interface between the open tip and the distal edge comprising a substantially straight cutting edge.

* * * * *